United States Patent [19]

Canich

[11] Patent Number: 6,160,066
[45] Date of Patent: Dec. 12, 2000

[54] MONOCYCLOPENTADIENYL METAL COMPOUNDS FOR ETHYLENE-α-OLEFIN-COPOLYMER PRODUCTION CATALYSTS

[75] Inventor: Jo Ann Marie Canich, Webster, Tex.

[73] Assignee: Exxon Chemical Patents, Inc., Baytown, Tex.

[21] Appl. No.: 09/243,722

[22] Filed: Feb. 3, 1999

Related U.S. Application Data

[62] Division of application No. 08/487,255, Jun. 6, 1995, Pat. No. 5,955,625, which is a continuation of application No. 08/412,810, Mar. 29, 1995, abandoned, which is a continuation-in-part of application No. 08/265,533, Jun. 24, 1994, abandoned, which is a continuation-in-part of application No. 08/466,547, Jun. 6, 1995, abandoned.

[51] Int. Cl.$^7$ ...................................................... C08F 4/00
[52] U.S. Cl. ......................... 526/160; 526/127; 526/943; 526/352; 526/348; 526/161; 502/152; 502/155
[58] Field of Search ..................... 526/127, 160, 526/943, 352, 348; 502/152, 155

[56] References Cited

U.S. PATENT DOCUMENTS

| | | |
|---|---|---|
| 4,048,423 | 9/1977 | MacLeay et al. . |
| 4,668,823 | 5/1987 | Murray . |
| 5,041,584 | 8/1991 | Crapo et al. . |
| 5,055,438 | 10/1991 | Canich . |
| 5,057,475 | 10/1991 | Canich et al. . |
| 5,057,478 | 10/1991 | Abe et al. . |
| 5,064,802 | 11/1991 | Stevens et al. . |
| 5,096,867 | 3/1992 | Canich . |
| 5,153,157 | 10/1992 | Hlatky et al. . |
| 5,198,401 | 3/1993 | Turner et al. . |
| 5,264,405 | 11/1993 | Canich . |
| 5,278,119 | 1/1994 | Turner et al. . |
| 5,317,036 | 5/1994 | Brady, III et al. . |
| 5,321,106 | 6/1994 | LaPointe ................................. 526/126 |
| 5,516,848 | 5/1996 | Canich et al. . |
| 5,539,056 | 7/1996 | Yang et al. . |

FOREIGN PATENT DOCUMENTS

| | | |
|---|---|---|
| 0 416 815 A2 | 3/1991 | European Pat. Off. . |
| 0 561 476 A1 | 9/1993 | European Pat. Off. . |
| WO 94/07928 | 4/1994 | WIPO . |

*Primary Examiner*—David W. Wu
*Assistant Examiner*—Ling-Siu Choi
*Attorney, Agent, or Firm*—William G. Muller

[57] ABSTRACT

Described are certain monocyclopentadienyl Group IV B metal compounds, catalyst systems comprising such monocyclopentadienyl metal compounds and an activator, and a process using such catalyst systems for the production of polyolefins, particularly high molecular weight ethylene-α-olefin copolymers having a high level of α-olefin incorporation.

8 Claims, No Drawings

MONOCYCLOPENTADIENYL METAL COMPOUNDS FOR ETHYLENE-α-OLEFIN-COPOLYMER PRODUCTION CATALYSTS

This is a division of U.S. Ser. No. 08/487,255, filed Jun. 6, 1995, U.S. Pat. No. 5,955,825; which is a continuation of U.S. Ser. No. 08/412,810 filed Mar. 29, 1995; abandoned, which is a continuation-in-part of 08/265,533 filed Jun. 24, 1994, abandoned, which is a C-I-P of Ser. No. 08/466,547 filed Jun. 6, 1995, abandoned.

FIELD OF THE INVENTION

This invention relates to certain monocyclopentadienyl metal compounds, to certain catalyst systems comprising such monocyclopentadienyl metal compounds along with an activator, and to a process using such catalyst systems for production of polyolefins, particularly high molecular weight ethylene-α-olefin copolymers having a high level of α-olefin comonomer incorporation.

BACKGROUND OF THE INVENTION

As is well known, various processes and catalysts exist for homopolymerization or copolymerization of olefins. For many applications it is of primary importance for a polyolefin to have a high weight average molecular weight while having a relatively narrow molecular weight distribution. A high weight average molecular weight, when accompanied by a narrow molecular weight distribution, provides a polyolefin or an ethylene-α-olefin copolymer with high strength properties.

U.S. Pat. No. 5,264,504 discloses certain monocyclopentadienyl metal compounds having an amido radical with an aliphatic or alicyclic hydrocarbyl moiety attached thereto through a primary or secondary carbon atom. EPO 416,815 discloses certain monocyclopentadienyl metal compounds which are activated with an alumoxane co-catalyst. U.S. Pat. No. 5,064,802 discloses certain monocyclopentadienyl metal compounds which are activated with a non-coordinating compatible anion of a Bronsted acid salt.

SUMMARY OF THE INVENTION

The present invention is directed to certain monocyclopentadienyl compounds and to catalyst systems which include such monocyclopentadienyl metal compounds along with an activator component. The catalyst systems of the present invention are highly productive for polymerizing ethylene and olefins to produce high molecular weight copolymers having a high content of α-olefin comonomer. More particularly, the present invention relates to certain monocyclopentadienyl metal compounds which include an amido moiety having an alicyclic hydrocarbyl moiety covalently bonded thereto through a tertiary carbon atom. A tertiary carbon atom is defined here as a carbon atom bonded to three other non-hydrogen atoms.

DETAILED DESCRIPTION OF THE INVENTION

This invention relates to the discovery of certain monocyclopentadienyl metal compounds which, by reason of the presence therein of ligands of a particular nature, are particularly useful in catalyst systems to provide greatly improved performance characteristics. The monocyclopentadienyl metal compounds of the present invention are represented by the formula:

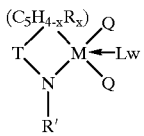

Formula I wherein: M is Zr, Hf or Ti;

$(C_5H_{4-x}R_x)$ is a cyclopentadienyl ring which is substituted with from zero to four substituent groups R, "x" is 0, 1, 2, 3, or 4 denoting the degree of substitution, and each substituent group R is, independently, a radical selected from $C_1$–$C_{20}$ hydrocarbyl radicals, substituted $C_1$–$C_{20}$ hydrocarbyl radicals wherein one or more hydrogen atoms is replaced by a halogen radical, an amido radical, a phosphido radical, an alkoxy radical, an aryloxy radical or any other radical containing a Lewis acidic or basic functionality; $C_1$–$C_{20}$ hydrocarbyl-substituted metalloid radicals wherein the metalloid is selected from the Group IV A of the Periodic Table of Elements; halogen radicals; amido radicals; phosphido radicals; alkoxy radicals; alkylborido radicals; or any other radical containing Lewis acidic or basic functionality; or $(C_5H_{4-x}R_x)$ is a cyclopentadienyl ring in which at least two adjacent R-groups are joined together and along with the carbon atoms to which they are attached form a $C_4$–$C_{20}$ ring system;

R' is a radical selected from $C_4$–$C_{30}$, preferably $C_4$–$C_{20}$, alicyclic hydrocarbyl radicals wherein one or more hydrogen atoms may be replaced by radicals containing Lewis acidic or basic functionalities such as, for example, radicals selected from halogen, amido, phosphido, alkoxy, aryloxy and the like, with the proviso that R' is covalently bonded to the nitrogen atom through a tertiary carbon atom;

each Q is independently a radical selected from halide; hydride; substituted or unsubstituted $C_1$–$C_{20}$ hydrocarbyl; alkoxide; aryloxide; amide; or phospide; or both Q together may be an alkylidene or a cyclometallated hydrocarbyl or any other divalent anionic chelating ligand, with the proviso that where any Q is a hydrocarbyl radical, such Q is not a substituted or unsubstituted cyclopentadienyl radical;

T is a covalent bridging group containing a Group IV A or V A element such as, but not limited to, a dialkyl, dialicyclyl, alkylalicyclyl, arylalicyclyl, alkylaryl or diaryl silicon or germanium radical; alkyl and/or aryl phosphine or amine radical; or a substituted or unsubstituted hydrocarbyl radical such as methylene, ethylene and the like which may be substituted with substituents selected from alkyl, alicyclyl and aryl radicals or combinations thereof having from 1 to 20 carbon atoms and silyl atoms.

Such compounds can also include an $L_w$ complexed thereto wherein L is a neutral Lewis base. Examples of such neutral Lewis bases include but are not limited to diethylether, tetraethylammonium chloride, tetrahydrofuran, dimethylaniline, aniline, trimethylphosphine, n-butylamine, and the like. The "w" is a number from 0 to 3. Optionally, L may be covalently bonded to one or both Q provided Q is not hydride or halide.

L can also be a second transition metal compound of the same type such that the two metal centers M and M' are bridged by Q and Q', wherein M' has the same meaning as M, and Q' has the same meaning as Q. Such dimeric compounds are represented by the formula:

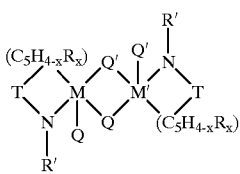

Formula II

A preferred class of compounds of the present invention are represented by the formula:

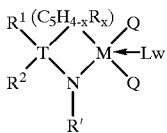

Formula III wherein:

M is selected from Ti, Hf and Zr;

$(C_5H_{4-x}R_x)$ is as defined above with respect to Formula I;

each of $R^1$ and $R^2$ are independently selected from $C_1$–$C_{20}$ hydrocarbyl radicals, and may optionally be joined together to form a cyclic ring structure;

T is Si or Ge;

each Q is independently selected from halide, hydride, substituted or unsubstituted $C_1$–$C_{20}$ hydrocarbyl radicals; alkoxide; amide; and phosphide radicals, with the proviso that Q is not a substituted or unsubstituted cyclopentadienyl radical;

R' is selected from $C_4$–$C_{20}$ alicyclic hydrocarbyl radicals with the proviso that R' is covalently bonded to the nitrogen atom through a tertiary carbon atom; and $L_w$ is optional and is as defined above.

A more preferred class of compounds of the present invention are those compounds represented by Formula IV:

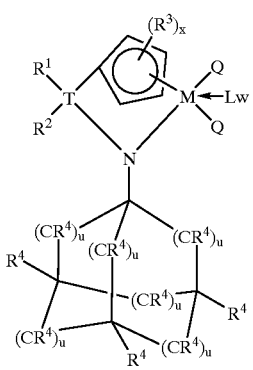

Formula IV wherein:

M is selected from Ti, Zr and Hf;

T is selected from Si or Ge;

each of $R^1$ and $R^2$ is independently selected from $C_1$–$C_{20}$ alkyl, $C_6$–$C_{22}$ aryl, $C_3$–$C_{20}$ cycloalkyl radicals or combinations thereof and may optionally be joined together to form a cyclic ring structure;

each $R^3$ is independently selected from hydrogen; $C_1$–$C_{20}$ alkyl; $C_3$–$C_{20}$ cycloalkyl; $C_6$–$C_{22}$ aryl; halogen; amido; phosphido; alkoxy; aryloxy; alkylborido; and the like radicals; or combinations thereof;

each Q is independently selected from hydrogen; halogen; $C_1$–$C_{20}$ alkyl; $C_6$–$C_{22}$ aryl; $C_3$–$C_{20}$ cycloalkyl; alkoxy; aryloxy; amido; and phosphido radicals or combinations thereof;

u is an integer of from 0 to 6, preferably 0 to 4, such as from 1 to 3;

x is 0–4;

each $R^4$ is independently selected from hydrogen; halogen, $C_1$–$C_{10}$ alkyl; $C_3$–$C_{10}$ cycloalkyl; $C_6$–$C_{22}$ aryl; amido; alkoxy; aryloxy; or combinations thereof and the like radicals; or two $R^4$ groups along with the carbon atom or atoms to which they are attached, form a saturated or partially saturated alicyclic group or form an aryl group; and Lw is optional and is as defined above.

Preferred compounds within the scope of Formula IV are those wherein each $R^3$ is independently selected from $C_1$–$C_{20}$ alkyl; $C_3$–$C_{20}$ cycloalkyl; $C_6$–$C_{22}$ aryl; or combinations thereof; and M is titanium. As utilized herein, the term "alkyl", alone or in combination, means a straight-chain or branched-chain alkyl radical containing from 1 to about 20, preferably from 1 to about 10 carbon atoms. Examples of such radicals include methyl, ethyl, n-propyl, iso-propyl, n-butyl, iso-butyl, sec-butyl, tert-butyl, pentyl, iso-amyl, hexyl, octyl, decyl, dodecyl, and the like. Such alkyl and alicyclic radicals may carry one or more substitutes selected from alkoxy, halo, aryloxy, hydroxy, amino, phosphino, borido, nitro and the like. The term "alkoxy", alone or in combination means an alkyl oxy radical wherein the term "alkyl" is as defined above. Examples of suitable alkoxy radicals include methoxy, ethoxy, n-proxy, iso-propoxy, n-butoxy, sec-butoxy, tert-butoxy, pentoxy and the like. The term "alicyclic", alone or in combination, means a branched or unbranched cyclic alkyl radical as defined above which is saturated, or partially saturated. Examples of such alicyclic radicals include cyclopropyl, cyclobutyl, cyclohexyl, cyclododecyl, 2-methylcyclohexyl, norbornyl, adamantyl and the like. The term "aryl", alone or in combination, means a mono, bi or poly aromatic radical. Examples of such radicals include phenyl, cycloheptatrienyl, naphthyl, anthracenyl, chrysenyl, azulenyl, biphenyl, p-terphenyl, 1-phenyl naphethyl and the like. Such aryl radicals may carry one or more substituents selected from alkyl, alkoxy, aryloxy, halogen, hydroxy, amino, phosphido, borido, nitro and the like. Examples of such substituted aryl radicals include p-tolyl, 4-methoxyphenyl, 4t-butylphenyl and the like. The term "aryloxy", alone or in combination, means an aryl oxy radical wherein aryl is as defined above. Examples include phenoxy and the like. The term "halogen" or "halo" means fluoride, chloride, bromide or iodide radicals. The term "ring system" means a bi- or polycyclic system wherein one or more aromatic radicals is fused to one or more alicyclic and/or aryl radicals. Examples of such ring systems include fluorenyl, indenyl, tetrahydroindenyl, benzindenyl, and the like which systems may be substituted with one or more radicals such as alkyl radicals.

A tertiary (30) carbon atom means a carbon atom which is bonded to three other non-hydrogen atoms. An alicyclic hydrocarbyl radical bonded to a nitrogen atom through a tertiary carbon atom means that the tertiary carbon atom is a member of the alicyclic radical and is bonded to three other non-hydrogen atoms, such as to three carbon atoms. Examples of such radicals include 1-adamantyl, 3-noradamantyl, 1-norbornyl, 1-triptycenyl, 1-tricyclo $[5.2.1.0^{2,6}]$decyl, 4tricyclo$[2.2.1.0^{2,6}]$heptyl, and the like. The term "hydrocarbyl" means a radical derived from a hydrocarbon. Preferred hydrocarbyl radicals are those containing from 1–20 carbon atoms. Examples of such radicals include alkyl, aryl, cycloalkyl radicals or combinations thereof. Preferred radicals are $C_1$–$C_{20}$ alkyl, $C_6$–$C_{22}$ aryl, and $C_3$–$C_{20}$ cycloalkyl radicals, or combinations thereof.

A more preferred class of compounds are those compounds represented by the above Formula IV wherein M is Ti. A most preferred class of compounds are those represented by the above Formula IV wherein M is Ti and wherein $R_1$ and $R_2$ are independently selected from $C_1$–$C_6$ alkyl radicals, $C_6$–$C_{12}$ aryl radicals, $C_3$–$C_{12}$ cycloalkyl radicals, and combinations thereof.

Examples of specific compounds within the classes of compounds defined by Formula IV include:

dimethylsilyl(tetramethylcyclopentadienyl)-(1-adamantylamido)titanium dimethyl;

dimethylsilyl(tetramethylcyclopentadienyl)-(3-noradamantanylamido)titanium dimethyl;

dimethylsily(tetramethylcyclopentadienyl)-(3,5-dimethyl-1-adamantylamido)titanium dimethyl;

dimethylsilyl(tetramethylcyclopentadienyl)-(3-fluoro-1-adamantylamido)titanium dimethyl;

dimethylsilyl(tetramethylcyclopentadienyl)-(4-tricyclo[2.2.1.0$^{2,6}$]heptylamido)titanium dimethyl;

dimethylsilyl(tetramethylcyclopentadienyl)-(3-methyl-1-adamantyl)titanium dimethyl;

dimethylsilyl(tetramethylcyclopentadienyl)-(3,5,7-trimethyladamantyl)titanium dimethyl;

methylphenylsilyl(tetramethylcyclopentadienyl)-(1-adamantylamido)titanium dimethyl;

methylphenylsilyl(tetramethylcyclopentadienyl)-(3-noradamantanylamido)titanium dimethyl;

methylphenylsilyl(tetramethylcyclopentadienyl)-(3,5-dimethyl-1-adamantylamido)titanium dimethyl;

methylphenylsilyl(tetramethylcyclopentadienyl)-(3-methyl-adamantylamido)titanium dimethyl methylphenylsilyl(tetramethylcyclopentadienyl)-(3,5,7-trimethyladamantylamido)titanium dimethyl methylphenylsilyl(tetramethylcyclopentadienyl)-(3-fluoro-1-adamantylamido)titanium dimethyl;

methylphenylsilyl(tetramethylcyclopentadienyl)-(4-tricyclo[2.2.1.0$^{2,6}$]heptylamido)titanium dimethyl;

diphenylsilyl(tetramethylcyclopentadienyl)-(1-adamantylamido)titanium dimethyl;

diphenylsilyl(tetramethylcyclopentadienyl)-(3-noradamantanylamido)titanium dimethyl;

diphenylsilyl(tetramethylcyclopentadienyl)-(3,5-dimethyl-1-adamantylamido)titanium dimethyl;

diphenylsilyl(tetramethylcyclopentadienyl)-(3-methyl-1-adamantylamido)titanium dimethyl;

diphenylsilyl(tetramethylcyclopentadienyl)-( 3,5,7trimethyl-1-adamantylamido)titanium dimethyl;

diphenylsilyl(tetramethylcyclopentadienyl)-(3-fluoro-1-adamantylamido)titanium dimethyl;

diphenylsilyl(tetramethylcyclopentadienyl)-(4-tricyclo[2.2.1.0$^{2,6}$]heptylamido)titanium dimethyl;

dimethylsilyl(tetramethylcyclopentadienyl)-(1-adamantylamido)titanium diphenyl;

dimethylsilyl(tetramethylcyclopentadienyl)-(3-noradamantanylamido)titanium diphenyl;

dimethylsilyl(tetramethylcyclopentadienyl)-(3,5-dimethyl-1-adamantylamido)titanium diphenyl;

dimethylsilyl(tetramethylcyclopentadienyl)-(3-methyl-1-adamantylamido)titanium diphenyl;

dimethylsilyl(tetramethylcyclopentadienyl)-(3,5,7-trimethyl-1-adamantylamido)titanium diphenyl;

dimethylsilyl(tetramethylcyclopentadienyl)-(3-fluoro-1-adamantylamido)titanium diphenyl;

dimethylsilyl(tetramethylcyclopentadienyl)-(4-tricyclo[2.2.1.0$^{2,6}$]heptylamido)titanium diphenyl;

methylphenylsilyl(tetramethylcyclopentadienyl)-(1-adamantylamido)titanium diphenyl;

methylphenylsilyl(tetramethylcyclopentadienyl)-(3-noradamantanylamido)titanium diphenyl;

methylphenylsilyl(tetramethylcyclopentadienyl)-(3,5-dimethyl-1-adamantylamido)titanium diphenyl;

methylphenylsilyl(tetramethylcyclopentadienyl)-(3-methyl-1-adamantylamido)titanium diphenyl;

methylphenylsilyl(tetramethylcyclopentadienyl)-(3,5,7-trimethyl-1-adamantylamido)titanium diphenyl;

methylphenylsilyl(tetramethylcyclopentadienyl)-(3-fluoro-1-adamantylamido)titanium diphenyl;

methylphenylsilyl(tetramethylcyclopentadienyl)-(4-tricyclo[2.2.1.0$^{2,6}$]heptylamido)titanium diphenyl;

diphenylsilyl(tetramethylcyclopentadienyl)-(1-adamantylamido)titanium diphenyl;

diphenylsilyl(tetramethylcyclopentadienyl)-(3-noradamantanylamido)titanium diphenyl;

diphenylsilyl(tetramethylcyclopentadienyl)-(3,5-dimethyl-1-adamantylamido)titanium diphenyl;

diphenylsilyl(tetramethylcyclopentadienyl)-(3-methyl-1-adamantylamido)titanium diphenyl;

diphenylsilyl(tetramethylcyclopentadienyl)-(3,5,7-trimethyl-1-adamantylamido)titanium diphenyl;

diphenylsilyl(tetramethylcyclopentadienyl)-(3-fluoro-1-adamantylamido)titanium diphenyl;

diphenylsilyl(tetramethylcyclopentadienyl)-(4-tricyclo[2.2.1.0$^{2,6}$]heptylamido)titanium diphenyl;

dimethylsilyl(tetramethylcyclopentadienyl)-(1-adamantylamido)hafnium dimethyl;

dimethylsilyl(tetramethylcyclopentadienyl)-(3-noradamantanylamido)hafnium dimethyl;

dimethylsilyl(tetramethylcyclopentadienyl)-(3,5-dimethyl-1-adamantylamido)hafnium dimethyl;

dimethylsilyl(tetramethylcyclopentadienyl)-(3-methyl-1-adamantylamido)hafnium dimethyl;

dimethylsilyl(tetramethylcyclopentadienyl)-(3,5,7-trimethyl-1-adamantylamido)hafnium dimethyl;

dimethylsilyl(tetramethylcyclopentadienyl)-(3-fluoro-1-adamantylamido)hafnium dimethyl;

dimethylsilyl(tetramethylcyclopentadienyl)-(4-tricyclo[2.2.1.0$^{2,6}$]heptylamido)hafnium dimethyl;

methylphenylsilyl(tetramethylcyclopentadienyl)-(1-adamantylamido)hafnium dimethyl;

methylphenylsilyl(tetramethylcyclopentadienyl)-(3-noradamantanylamido)hafnium dimethyl;

methylphenylsilyl(tetramethylcyclopentadienyl)-(3,5-dimethyl-1-adamantylamido)hafnium dimethyl;

methylphenylsilyl(tetramethylcyclopentadienyl)-(3-methyl-1-adamantylamido)hafnium dimethyl;

methylphenylsilyl(tetramethylcyclopentadienyl)-(3,5,7-trimethyl-1-adamantylamido)hafnium dimethyl;

methylphenylsilyl(tetramethylcyclopentadienyl)-(3-fluoro-1-adamantylamido)hafnium dimethyl;

methylphenylsilyl(tetramethylcyclopentadienyl)-(4tricyclo[2.2.1.0$^{2,6}$]heptylamido)hafnium dimethyl;

diphenylsilyl(tetramethylcyclopentadienyl)-(1-adamantylamido)hafnium dimethyl;
diphenylsilyl(tetramethylcyclopentadienyl)-(3-noradamantanylamido)hafnium dimethyl;
diphenylsilyl(tetramethylcyclopentadienyl)-(3,5-dimethyl-1-adamantylamido)hafnium dimethyl;
diphenylsilyl(tetramethylcyclopentadienyl)-(3-methyl-1-adamantylamido)hafnium dimethyl;
diphenylsilyl(tetramethylcyclopentadienyl)-(3,5,7-trimethyl-1-adamantylamido)hafnium dimethyl;
diphenylsilyl(tetramethylcyclopentadienyl)-(3-fluoro-1-adamantylamido)hafnium dimethyl;
diphenylsilyl(tetramethylcyclopentadienyl)-(4tricyclo[2.2.1.0$^{2,6}$]heptylamido)hafnium dimethyl;
dimethylsilyl(tetramethylcyclopentadienyl)-(1-adamantylamido)hafnium diphenyl;
dimethylsilyl(tetramethylcyclopentadienyl)-(3-noradamantanylamido)hafnium diphenyl;
dimethylsilyl(tetramethylcyclopentadienyl)-(3,5-dimethyl-1-adamantylamido)hafnium diphenyl;
dimethylsilyl(tetramethylcyclopentadienyl)-(3-methyl-1-adamantylamido)hafnium diphenyl;
dimethylsilyl(tetramethylcyclopentadienyl)-(3,5,7-trimethyl-1-adamantylamido)hafnium diphenyl;
dimethylsilyl(tetramethylcyclopentadienyl)-(3-fluoro-1-adamantylamido)hafnium diphenyl;
dimethylsilyl(tetramethylcyclopentadienyl)-(4-tricyclo[2.2.1.0$^{2,6}$]heptylamido)hafnium diphenyl;
methylphenylsilyl(tetramethylcyclopentadienyl)-(1-adamantylamido)hafnium diphenyl;
methylphenylsilyl(tetramethylcyclopentadienyl)-(3-noradamantanylamido)hafnium diphenyl;
methylphenylsilyl(tetramethylcyclopentadienyl)-(3,5-dimethyl-1-adamantylamido)hafnium diphenyl;
methylphenylsilyl(tetramethylcyclopentadienyl)-(3-methyl-1-adamantylamido)hafnium diphenyl;
methylphenylsilyl(tetramethylcyclopentadienyl)-(3,5,7-trimethyl-1-adamantylamido)hafnium diphenyl;.
methylphenylsilyl(tetramethylcyclopentadienyl)-(3-fluoro-1-adamantylamido)hafnium diphenyl;
methylphenylsilyl(tetramethylcyclopentadienyl)-(4-tricyclo[2.2.1.0$^{2,6}$]heptylamido)hafnium diphenyl;
diphenylsilyl(tetramethylcyclopentadienyl)-(1-adamantylamido)hafnium diphenyl;
diphenylsilyl(tetramethylcyclopentadienyl)-(3-noradamantanylamido)hafnium diphenyl;
diphenylsilyl(tetramethylcyclopentadienyl)-(3,5-dimethyl-1-adamantylamido)hafnium diphenyl;
diphenylsily(tetramethylcyclopentadienyl)-(3-methyl-1-adamantylamido)hafnium diphenyl;
diphenylsilyl(tetramethylcyclopentadienyl)-(3,5,7-trimethyl-1-adamantylamido)hafnium diphenyl;
diphenylsilyl(tetramethylcyclopentadienyl)-(3-fluoro-1-adamantylamido)hafnium diphenyl;
diphenylsilyl(tetramethylcyclopentadienyl)-(4-tricyclo[2.2.1.0$^{2,6}$]heptylamido)hafnium diphenyl;
dimethylsilyl(tetramethylcyclopentadienyl)-(1-adamantylamido)zirconium dimethyl;
dimethylsilyl(tetramethylcyclopentadienyl)-(3-noradamantanylamido)zirconium dimethyl;
dimethylsilyl(tetramethylcyclopentadienyl)-(3,5-dimethyl-1-adamantylamido)zirconium dimethyl;
dimethylsilyl(tetramethylcyclopentadienyl)-(3-methyl-1-adamantylamido)zirconium dimethyl;
dimethylsilyl(tetramethylcyclopentadienyl)-(3,5,7-trimethyl-1-adamantylamido)zirconium dimethyl;
dimethylsilyl(tetramethylcyclopentadienyl)-(3-fluoro-1-adamantylamido)zirconium dimethyl;
dimethylsilyl(tetramethylcyclopentadienyl)-(4-tricyclo[2.2.1.0$^{2,6}$]heptylamido)zirconium dimethyl;
methylphenylsilyl(tetramethylcyclopentadienyl)-(1-adamantylamido)zirconium dimethyl;
methylphenylsilyl(tetramethylcyclopentadienyl)-(3-noradamantanylamido)zirconium dimethyl;
methylphenylsilyl(tetramethylcyclopentadienyl)-(3,5-dimethyl-1-adamantylamido)zirconium dimethyl;
methylphenylsilyl(tetramethylcyclopentadienyl)-(3-methyl-1-adamantylamido)zirconium dimethyl;
methylphenylsilyl(tetramethylcyclopentadienyl)-(3,5,7-trimethyl-1-adamantylamido)zirconium dimethyl;
methylphenylsilyl(tetramethylcyclopentadienyl)-(3-fluoro-1-adamantylamido)zirconium dimethyl;
methylphenylsilyl(tetramethylcyclopentadienyl)-(4-tricyclo[2.2.1.0$^{2,6}$]heptylamido)zirconium dimethyl;
diphenylsilyl(tetramethylcyclopentadienyl)-(1-adamantylamido)zirconium dimethyl;
diphenylsilyl(tetramethylcyclopentadienyl)-(3-noradamantanylamido)zirconium dimethyl;
diphenylsilyl(tetramethylcyclopentadienyl)-(3,5-dimethyl-1-adamantylamido)zirconium dimethyl;
diphenylsilyl(tetramethylcyclopentadienyl)-(3-methyl-1-adamantylamido)zirconium dimethyl;
diphenylsilyl(tetramethylcyclopentadienyl)-(3,5,7-trimethyl-1-adamantylamido)zirconium dimethyl;
diphenylsilyl(tetramethylcyclopentadienyl)-(3-fluoro-1-adamantylamido)zirconium dimethyl;
diphenylsilyl(tetramethylcyclopentadienyl)-(4-tricyclo[2.2.1.0$^{2,6}$]heptylamido)zirconium dimethyl;
dimethylsilyl(tetramethylcyclopentadienyl)-(1-adamantylamido)zirconium diphenyl;
dimethylsilyl(tetramethylcyclopentadienyl)-(3-noradamantanylamido)zirconium diphenyl;
dimethylsilyl(tetramethylcyclopentadienyl)-(3,5-dimethyl-1-adamantylamido)zirconium diphenyl;
dimethylsilyl(tetramethylcyclopentadienyl)-(3-methyl-1-adamantylamido)zirconium diphenyl;
dimethylsilyl(tetramethylcyclopentadienyl)-(3,5,7-trimethyl-1-adamantylamido)zirconium diphenyl;
dimethylsilyl(tetramethylcyclopentadienyl)-(3-fluoro-1-adamantylamido)zirconium diphenyl;
dimethylsilyl(tetramethylcyclopentadienyl)-(4-tricyclo[2.2.1.0$^{2,6}$]heptylamido)zirconium diphenyl;
methylphenylsilyl(tetramethylcyclopentadienyl)-(1-adamantylamido)zirconium diphenyl;
methylphenylsilyl(tetramethylcyclopentadienyl)-(3-noradamantanylamido)zirconium diphenyl;
methylphenylsilyl(tetramethylcyclopentadienyl)-(3,5-dimethyl-1-adamantylamido)zirconium diphenyl;
methylphenylsilyl(tetramethylcyclopentadienyl)-(3-methyl-1-adamantylamido)zirconium diphenyl;
methylphenylsilyl(tetramethylcyclopentadienyl)-(3,5,7-trimethyl-1-adamantylamido)zirconium diphenyl;
methylphenylsilyl(tetramethylcyclopentadienyl)-(3-fluoro-1-adamantylamido)zirconium diphenyl;

methylphenylsilyl(tetramethylcyclopentadienyl)-(4-tricyclo[2.2.1.0$^{2,6}$]heptylamido)zirconium diphenyl;
diphenylsilyl(tetramethylcyclopentadienyl)-(1-adamantylamido)zirconium diphenyl;
diphenylsilyl(tetramethylcyclopentadienyl)-(3-noradamantanylamido)zirconium diphenyl;
diphenylsilyl(tetramethylcyclopentadienyl)-(3,5-dimethyl-1-adamantylamido)zirconium diphenyl;
diphenylsilyl(tetramethylcyclopentadienyl)-(3-methyl-1-adamantylamido)zirconium diphenyl;
diphenylsilyl(tetramethylcyclopentadienyl)-(3,5,7-trimethyl-1-adamantylamido)zirconium diphenyl;
diphenylsilyl(tetramethylcyclopentadienyl)-(3-fluoro-1-adamantylamido)zirconium diphenyl;
diphenylsilyl(tetramethylcyclopentadienyl)-(4-tricyclo[2.2.1.0$^{2,6}$]heptylamido)zirconium diphenyl;
dimethylgermanyl(tetramethylcyclopentadienyl)-(1-adamantylamido)titanium dimethyl;
dimethylgermanyl(tetramethylcyclopentadienyl)-(3-noradamantanylamido)titanium dimethyl;
dimethylgermanyl(tetramethylcyclopentadienyl)-(3,5-dimethyl-1-adamantylamido)titanium dimethyl;
dimethylgermanyl(tetramethylcyclopentadienyl)-(3-methyl-1-adamantylamido)titanium dimethyl;
dimethylgermanyl(tetramethylcyclopentadienyl)-(3,5,7-trimethyl-1-adamantylamido)titanium dimethyl;
dimethylgermanyl(tetramethylcyclopentadienyl)-(3-fluoro-1-adamantylamido)titanium dimethyl;
dimethylgermanyl(tetramethylcyclopentadienyl)-(4-tricyclo[2.2.1.0$^{2,6}$]heptylamido)titanium dimethyl;
methylphenylgermanyl(tetramethylcyclopentadienyl)-(1-adamantylamido) titanium dimethyl;
methylphenylgermanyl(tetramethylcyclopentadienyl)-(3-noradamantanylamido)titanium dimethyl;
methylphenylgermanyl(tetramethylcyclopentadienyl)-(3,5-dimethyl-1-adamantylamido)titanium dimethyl;
methylphenylgermanyl(tetramethylcyclopentadienyl)-(3-methyl-1-adamantylamido)titanium dimethyl;
methylphenylgermanyl(tetramethylcyclopentadienyl)-(3,5,7-trimethyl-1-adamantylamido)titanium dimethyl;
methylphenylgermanyl(tetramethylcyclopentadienyl)-(3-fluoro-1-adamantylamido)titanium dimethyl;
methylphenylgermanyl(tetramethylcyclopentadienyl)-(4-tricyclo[2.2.1.0$^{2,6}$]heptylamido)titanium dimethyl;
diphenylgermanyl(tetramethylcyclopentadienyl)-(1-adamantylamido)titanium dimethyl;
diphenylgermanyl(tetramethylcyclopentadienyl)(3-noradamantanylamido)titanium dimethyl;
diphenylgermanyl(tetramethylcyclopentadienyl)-(3,5-dimethyl-1-adamantylamido)titanium dimethyl;
diphenylgermanyl(tetramethylcyclopentadienyl)-(3-methyl-1-adamantylamido)titanium dimethyl;
diphenylgermanyl(tetramethylcyclopentadienyl)-(3,5,7-trimethyl-1-adamantylamido)titanium dimethyl;
diphenylgermanyl(tetramethylcyclopentadienyl)-(3-fluoro-1-adamantylamido)titanium dimethyl;
diphenylgermanyl(tetramethylcyclopentadienyl)-(4-tricyclo[2.2.1.0$^{2,6}$]heptylamido)titanium dimethyl;
dimethylgermanyl(tetramethylcyclopentadienyl)-(1-adamantylamido)titanium diphenyl;
dimethylgermanyl(tetramethylcyclopentadienyl)-(3-noradamantanylamido)titanium diphenyl;
dimethylgermanyl(tetramethylcyclopentadienyl)-(3,5-dimethyl-1-adamantylamido)titanium diphenyl;
dimethylgermanyl(tetramethylcyclopentadienyl)-(3-methyl-1-adamantylamido)titanium diphenyl;
dimethylgermanyl(tetramethylcyclopentadienyl)-(3,5,7-trimethyl-1-adamantylamido)titanium diphenyl;
dimethylgermanyl(tetramethylcyclopentadienyl)-(3-fluoro-1-adamantylamido)titanium diphenyl;
dimethylgermanyl(tetramethylcyclopentadienyl)-(4-tricyclo [2.2.1.0$^{2,6}$]heptylamido)titanium diphenyl;
methylphenylgermanyl(tetramethylcyclopentadienyl)-(1-adamantylamido)titanium diphenyl;
methylphenylgermanyl(tetramethylcyclopentadienyl)-(3-noradamantanylamido)titanium diphenyl;
methylphenylgermanyl(tetramethylcyclopentadienyl)-(3,5-dimethyl-1-adamantylamido)titanium diphenyl;
methylphenylgermanyl(tetramethylcyclopentadienyl)-(3-methyl-1-adamantylamido)titanium diphenyl;
methylphenylgermanyl(tetramethylcyclopentadienyl)-(3,5,7-trimethyl-1-adamantylamido)titanium diphenyl;
methylphenylgermanyl(tetramethylcyclopentadienyl)-(3-fluoro-1-adamantylamido)titanium diphenyl;
methylphenylgermanyl(tetramethylcyclopentadienyl)-(4-tricyclo[2.2.1.0$^{2,6}$]heptylamido)titanium diphenyl;
diphenylgermanyl(tetramethylcyclopentadienyl)-(1-adamantylamido)titanium diphenyl;
diphenylgermanyl(tetramethylcyclopentadienyl)-(3-noradamantanylamido)titanium diphenyl;
diphenylgermanyl(tetramethylcyclopentadienyl)-(3,5-dimethyl-1-adamantylamido)titanium diphenyl;
diphenylgermanyl(tetramethylcyclopentadienyl)-(3-methyl-1-adamantylamido)titanium diphenyl;
diphenylgermanyl(tetramethylcyclopentadienyl)-(3,5,7-trimethyl-1-adamantylamido)titanium diphenyl;
diphenylgermanyl(tetramethylcyclopentadienyl)-(3-fluoro-1-adamantylamido)titanium diphenyl;
diphenylgermanyl(tetramethylcyclopentadienyl)-(4-tricyclo[2.2.1.0$^{2,6}$]heptylamido)titanium diphenyl;
dimethylgermanyl(tetramethylcyclopentadienyl)-(1-adamantylamido)hafnium dimethyl;
dimethylgermanyl(tetramethylcyclopentadienyl)-(3-noradamantanylamido)hafnium dimethyl;
dimethylgermanyl(tetramethylcyclopentadienyl)-(3,5-dimethyl-1-adamantylamido)hafnium dimethyl;
dimethylgermanyl(tetramethylcyclopentadienyl)-(3-methyl-1-adamantylamido)hafnium dimethyl;
dimethylgermanyl(tetramethylcyclopentadienyl)-(3,5,7-trimethyl-1-adamantylamido)hafnium dimethyl;
dimethylgermanyl(tetramethylcyclopentadienyl)-(3-fluoro-1-adamantylamido)hafnium dimethyl;
dimethylgermanyl(tetramethylcyclopentadienyl)-(4tricyclo[2.2.1.0$^{2,6}$]heptylamido)titanium diphenyl;
methylphenylgermanyl(tetramethylcyclopentadienyl)-(1-adamantylamido)hafnium dimethyl;
methylphenylgermanyl(tetramethylcyclopentadienyl)-(3-noradamantanylamido)hafnium dimethyl;
methylphenylgermanyl(tetramethylcyclopentadienyl)-(3,5-dimethyl-1-adamantylamido)hafnium dimethyl;
methylphenylgermanyl(tetramethylcyclopentadienyl)-(3-methyl-1-adamantylamido)hafnium dimethyl;
methylphenylgermanyl(tetramethylcyclopentadienyl)-(3,5,7-trimethyl-1-adamantylamido)hafnium dimethyl;

methylphenylgermanyl(tetramethylcyclopentadienyl)-(3-fluoro-1-adamantylamido)hafnium dimethyl;
methylphenylgermanyl(tetramethylcyclopentadienyl)-(4-tricyclo[2.2.1.0$^{2,6}$]heptylamido)hafnium dimethyl;
diphenylgermanyl(tetramethylcyclopentadienyl)-(1-adamantylamido)hafnium dimethyl;
diphenylgermanyl(tetramethylcyclopentadienyl)-(3-noradamantylamido)hafnium dimethyl;
diphenylgermanyl(tetramethylcyclopentadienyl)-(3,5-dimethyl-1-adamantylamido)hafnium dimethyl;
diphenylgermanyl(tetramethylcyclopentadienyl)-(3-methyl-1-adamantylamido)hafnium dimethyl;
diphenylgermanyl(tetramethylcyclopentadienyl)-(3,5,7-trimethyl-1-adamantylamido)hafnium dimethyl;
diphenylgermanyl(tetramethylcyclopentadienyl)-(3-fluoro-1-adamantylamido)hafnium dimethyl;
diphenylgermanyl(tetramethylcyclopentadienyl)-(4-tricyclo[2.2.1.0$^{2,6}$]heptylamido)hafnium dimethyl;
dimethylgermanyl(tetramethylcyclopentadienyl)-(1-adamantylamido)hafnium diphenyl;
dimethylgermanyl(tetramethylcyclopentadienyl)-(3-noradamantylamido)hafnium diphenyl;
dimethylgermanyl(tetramethylcyclopentadienyl)-(3,5-dimethyl-1-adamantylamido)hafnium diphenyl;
dimethylgermanyl(tetramethylcyclopentadienyl)-(3-methyl-1-adamantylamido)hafnium diphenyl;
dimethylgermanyl(tetramethylcyclopentadienyl)-(3,5,7-trimethyl-1-adamantylamido)hafnium diphenyl;
dimethylgermanyl(tetramethylcyclopentadienyl)-(3-fluoro-1-adamantylamido)hafnium diphenyl;
dimethylgermanyl(tetramethylcyclopentadienyl)-(4-tricyclo[2.2.1.0$^{2,6}$]heptylamido)hafnium diphenyl;
methylphenylgermanyl(tetramethylcyclopentadienyl)-(1-adamantylamido)hafnium diphenyl;
methylphenylgermanyl(tetramethylcyclopentadienyl)-(3-noradamantylamido)hafnium diphenyl;
methylphenylgermanyl(tetramethylcyclopentadienyl)-(3,5-dimethyl-1-adamantylamido)hafnium diphenyl;
methylphenylgermanyl(tetramethylcyclopentadienyl)-(3-methyl-1-adamantylamido)hafnium diphenyl;
methylphenylgermanyl(tetramethylcyclopentadienyl)-(3,5,7-trimethyl-1-adamantylamido)hafnium diphenyl;
methylphenylgermanyl(tetramethylcyclopentadienyl)-(3-fluoro-1-adamantylamido)hafnium diphenyl;
methylphenylgermanyl(tetramethylcyclopentadienyl)-(4-tricyclo[2.2.1.0$^{2,6}$]heptylamido)hafnium diphenyl;
diphenylgermanyl(tetramethylcyclopentadienyl)-(1-adamantylamido)hafnium diphenyl;
diphenylgermanyl(tetramethylcyclopentadienyl)-(3-noradamantylamido)hafnium diphenyl;
diphenylgermanyl(tetramethylcyclopentadienyl)-(3,5-dimethyl-1-adamantylamido)hafnium diphenyl;
diphenylgermanyl(tetramethylcyclopentadienyl)-(3-methyl-1-adamantylamido)hafnium diphenyl;
diphenylgermanyl(tetramethylcyclopentadienyl)-(3,5,7-trimethyl-1-adamantylamido)hafnium diphenyl;
diphenylgermanyl(tetramethylcyclopentadienyl)-(3-fluoro-1-adamantylamido)hafnium diphenyl;
diphenylgermanyl(tetramethylcyclopentadienyl)-(4-tricyclo[2.2.1.0$^{2,6}$]heptylamido)hafnium diphenyl;
dimethylgermanyl(tetramethylcyclopentadienyl)-(1-adamantylamido)zirconium dimethyl;
dimethylgermanyl(tetramethylcyclopentadienyl)-(3-noradamantylamido)zirconium dimethyl;
dimethylgermanyl(tetramethylcyclopentadienyl)-(3,5-dimethyl-1-adamantylamido)zirconium dimethyl;
dimethylgermanyl(tetramethylcyclopentadienyl)-(3-methyl-1-adamantylamido)zirconium dimethyl;
dimethylgermanyl(tetramethylcyclopentadienyl)-(3,5,7-trimethyl-1-adamantylamido)zirconium dimethyl;
dimethylgermanyl(tetramethylcyclopentadienyl)-(3-fluoro-1-adamantylamido)zirconium dimethyl;
dimethylgermanyl(tetramethylcyclopentadienyl)-(4-tricyclo[2.2.1.0$^{2,6}$]heptylamido)zirconium dimethyl;
methylphenylgermanyl(tetramethylcyclopentadienyl)-(1-adamantylamido)zirconium dimethyl;
methylphenylgermanyl(tetramethylcyclopentadienyl)-(3-noradamantylamido)zirconium dimethyl;
methylphenylgermanyl(tetramethylcyclopentadienyl)-(3,5-dimethyl-1-adamantylamido)zirconium dimethyl;
methylphenylgermanyl(tetramethylcyclopentadienyl)-(3-methyl-1-adamantylamido)zirconium dimethyl;
methylphenylgermanyl(tetramethylcyclopentadienyl)-(3,5,7-trimethyl-1-adamantylamido)zirconium dimethyl;
methylphenylgermanyl(tetramethylcyclopentadienyl)-(3-fluoro-1-adamantylamido)zirconium dimethyl;
methylphenylgermanyl(tetramethylcyclopentadienyl)-(4-tricyclo[2.2.1.0$^{2,6}$]heptylamido)zirconium dimethyl;
diphenylgermanyl(tetramethylcyclopentadienyl)-(1-adamantylamido)zirconium dimethyl;
diphenylgermanyl(tetramethylcyclopentadienyl)-(3-noradamantylamido)zirconium dimethyl;
diphenylgermanyl(tetramethylcyclopentadienyl)-(3,5-dimethyl-1-adamantylamido)zirconium dimethyl;
diphenylgermanyl(tetramethylcyclopentadienyl)-(3-methyl-1-adamantylamido)zirconium dimethyl;
diphenylgermanyl(tetramethylcyclopentadienyl)-(3,5,7-trimethyl-1-adamantylamido)zirconium dimethyl;
diphenylgermanyl(tetramethylcyclopentadienyl)-(3-fluoro-1-adamantylamido)zirconium dimethyl;
diphenylgermanyl(tetramethylcyclopentadienyl)-(4-tricyclo[2.2.1.0$^{2,6}$]heptylamido)zirconium dimethyl;
dimethylgermanyl(tetramethylcyclopentadienyl)-(1-adamantylamido)zirconium diphenyl;
dimethylgermanyl(tetramethylcyclopentadienyl)-(3-noradamantylamido)zirconium diphenyl;
dimethylgermanyl(tetramethylcyclopentadienyl)-(3,5-dimethyl-1-adamantylamido)zirconium diphenyl;
dimethylgermanyl(tetramethylcyclopentadienyl)-(3-methyl-1-adamantylamido)zirconium diphenyl;
dimethylgermanyl(tetramethylcyclopentadienyl)-(3,5,7-trimethyl-1-adamantylamido)zirconium diphenyl;
dimethylgermanyl(tetramethylcyclopentadienyl)-(3-fluoro-1-adamantylamido)zirconium diphenyl;
dimethylgermanyl(tetramethylcyclopentadienyl)-(4-tricyclo[2.2.1.0$^{2,6}$]heptylamido)zirconium diphenyl;
methylphenylgermanyl(tetramethylcyclopentadienyl)-(1-adamantylamido)zirconium diphenyl;
methylphenylgermanyl(tetramethylcyclopentadienyl)-(3-noradamantylamido)zirconium diphenyl;
methylphenylgermanyl(tetramethylcyclopentadienyl)-(3,5-dimethyl-1-adamantylamido)zirconium diphenyl;
methylphenylgermanyl(tetramethylcyclopentadienyl)-(3-methyl-1-adamantylamido)zirconium diphenyl;

methylphenylgermanyl(tetramethylcyclopentadienyl)-(3,
5,7-trimethyl-1-adamantylamido)zirconium diphenyl;
methylphenylgermanyl(tetramethylcyclopentadienyl)-(3-
fluoro-1-adamantylamido)zirconium diphenyl;
methylphenylgermanyl(tetramethylcyclopentadienyl)-(4-
tricyclo[2.2.1.0$^{2,6}$]heptylamido)zirconium diphenyl;
diphenylgermanyl(tetramethylcyclopentadienyl)-(1-
adamantylamido)zirconium diphenyl;
diphenylgermanyl(tetramethylcyclopentadienyl)-(3-
noradamantanylamido)zirconium diphenyl;
diphenylgermanyl(tetramethylcyclopentadienyl)-(3,5-
dimethyl-1-adamantylamido)zirconium diphenyl;
diphenylgermanyl(tetramethylcyclopentadienyl)-(3-
methyl-1-adamantylamido)zirconium diphenyl;
diphenylgermanyl(tetramethylcyclopentadienyl)-(3,5,7-
trimethyl-1-adamantylamido)zirconium diphenyl;
diphenylgermanyl(tetramethylcyclopentadienyl)-(3-
fluoro-1-adamantylamido)zirconium diphenyl;
diphenylgermanyl(tetramethylcyclopentadienyl)-(4-
tricyclo[2.2.1.0$^{2,6}$]heptylamido)zirconium diphenyl;

The above specific examples wherein each Q is methyl or each Q is phenyl is prepared from the corresponding compound wherein each Q is chloro. The dichloro (both Q are Cl) species of each of the above compounds are also within Formula II.

Another preferred class of compounds of the present invention are those compounds represented by the formula:

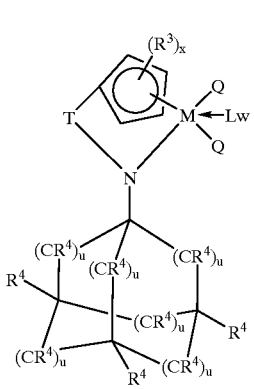

Formula V wherein $R^3$, $R^4$, Q, M, u, w, x, and L are as defined above; wherein T is selected from radicals of the formula $(CR^5R^6)_y$, wherein $R^5$ and $R^6$ are independently selected from hydrogen and $C_1$–$C_{20}$ hydrocarbyl radicals; and wherein y is 1, 2, or 3.

A more preferred class of compounds are those compounds represented by the above Formula V wherein M is Ti. A most preferred class of compounds are those represented by the above Formula V wherein M is Ti and wherein $R^5$ and $R^6$ are independently selected from hydrogen, $C_1$–$C_6$ alkyl radicals, $C_6$–$C_{12}$ aryl radicals, $C_3$–$C_{12}$ cycloalkyl radicals and combinations thereof.

Examples of specific compounds within the class of compounds defined by Formula V include:
methylene(tetramethylcyclopentadienyl)-(1-
adamantylamido)titanium dimethyl;
methylene(tetramethylcyclopentadienyl)-(
3-noradamantanylamido)titanium dimethyl;
methylene(tetramethylcyclopentadienyl)-(3,5-dimethyl-
1-adamantylamido)titanium dimethyl;
methylene(tetramethylcyclopentadienyl)-(3-methyl-1-
adamantylamido)titanium dimethyl;
methylene(tetramethylcyclopentadienyl)-(3,5,7-
trimethyl-1-adamantylamido)titanium dimethyl;
methylene(tetramethylcyclopentadienyl)-(3-fluoro-1-
adamantylamido)titanium dimethyl;
methylene(tetramethylcyclopentadienyl)-(4-tricyclo
[2.2.1.0$^{2,6}$]heptylamido)titanium dimethyl;
dimethylmethylene(tetramethylcyclopentadienyl)-(1-
adamantylamido)titanium dimethyl;
dimethylmethylene(tetramethylcyclopentadienyl)-(3-
noradamantanylamido)titanium dimethyl;
dimethylmethylene(tetramethylcyclopentadienyl)-(3,5-
dimethyl-1-adamantylamido)titanium dimethyl;
dimethylmethylene(tetramethylcyclopentadienyl)-(3-
methyl-1-adamantylamido)titanium dimethyl;
dimethylmethylene(tetramethylcyclopentadienyl)-(3,5,7-
trimethyl-1-adamantylamido)titanium dimethyl;
dimethylmethylene(tetramethylcyclopentadienyl)-(3-
fluoro-1-adamantylamido)titanium dimethyl;
dimethylmethylene(tetramethylcyclopentadienyl)-
(4tricyclo[2.2.1.0$^{2,6}$]heptylamido)titanium dimethyl;
diethylmethylene(tetramethylcyclopentadienyl)-(1-
adamantylamido)titanium dimethyl;
diethylmethylene(tetramethylcyclopentadienyl)-(3-
noradamantanylamido)titanium dimethyl;
diethylmethylene(tetramethylcyclopentadienyl)-(3,5-
dimethyl-1-adamantylamido)titanium dimethyl;
diethylmethylene(tetramethylcyclopentadienyl)-(3-
methyl-1-adamantylamido)titanium dimethyl;
diethylmethylene(tetramethylcyclopentadienyl)-( 3,5,7-
trimethyl-1-adamantylamido)titanium dimethyl;
diethylmethylene(tetramethylcyclopentadienyl)-(3-
fluoro-1-adamantylamido)titanium dimethyl;
diethylmethylene(tetramethylcyclopentadienyl)-(4-
tricyclo[2.2.1.0$^{2,6}$]heptylamido)titanium dimethyl;
ethylene(tetramethylcyclopentadienyl)-(1-
adamantylamido)titanium dimethyl;
ethylene(tetramethylcyclopentadienyl)-(3-
noradamantanylamido)titanium dimethyl;
ethylene(tetramethylcyclopentadienyl)-(3,5-dimethyl-1-
adamantylamido)titanium dimethyl;
ethylene(tetramethylcyclopentadienyl)-(3-methyl-1-
adamantylamido)titanium dimethyl;
ethylene(tetramethylcyclopentadienyl)-(3,5,7-trimethyl-
1-adamantylamido)titanium dimethyl;
ethylene(tetramethylcyclopentadienyl)-(3-fluoro-1-
adamantylamido)titanium dimethyl;
ethylene(tetramethylcyclopentadienyl)-(4-tricyclo
[2.2.1.0$^{2,6}$]heptylamido)titanium dimethyl;
1,1-dimethylethylene(tetramethylcyclopentadienyl)-(1-
adamantylamido)titanium dimethyl;
1,1-dimethylethylene(tetramethylcyclopentadienyl)-(3-
noradamantanylamido)titanium dimethyl;
1,1-dimethylethylene(tetramethylcyclopentadienyl)-(3,5-
dimethyl-1-adamantylamido)titanium dimethyl;
1,1-dimethylethylene(tetramethylcyclopentadienyl)-(3-
methyl-1-adamantylamido)titanium dimethyl;
1,1-dimethylethylene(tetramethylcyclopentadienyl)-(3,5,
7-trimethyl-1-adamantylamido)titanium dimethyl;
1,1-dimethylethylene(tetramethylcyclopentadienyl)-(3-
fluoro-1-adamantylamido)titanium dimethyl;
1,1-dimethylethylene(tetramethylcyclopentadienyl)-(4-
tricyclo[2.2.1.0$^{2,6}$]heptylamido)titanium dimethyl;

1,1-dipropylethylene(tetramethylcyclopentadienyl)-(1-adamantylamido)titanium dimethyl;
1,1-dipropylethylene(tetramethylcyclopentadienyl)-(3-noradamantanylamido)titanium dimethyl;
1,1-dipropylethylene(tetramethylcyclopentadienyl)-(3,5-dimethyl-1-adamantylamido)titanium dimethyl;
1,1-dipropylethylene(tetramethylcyclopentadienyl)-(3-methyl-1-adamantylamido)titanium dimethyl;
1,1-dipropylethylene(tetramethylcyclopentadienyl)-(3,5,7-trimethyl-1-adamantylamido)titanium dimethyl;
1,1-dipropylethylene(tetramethylcyclopentadienyl)-(3-fluoro-1-adamantylamido)titanium dimethyl;
1,1-dipropylethylene(tetramethylcyclopentadienyl)-(4-tricyclo[2.2.1.0$^{2,6}$]heptylamido)titanium dimethyl;
1,2-dimethylethylene(tetramethylcyclopentadienyl)-(1-adamantylamido)titanium dimethyl;
1,2-dimethylethylene(tetramethylcyclopentadienyl)-(3-noradamantanylamido)titanium dimethyl;
1,2-dimethylethylene(tetramethylcyclopentadienyl)-(3,5-dimethyl-1-adamantylamido)titanium dimethyl;
1,2-dimethylethylene(tetramethylcyclopentadienyl)-(3-methyl-1-adamantylamido)titanium dimethyl;
1,2-dimethylethylene(tetramethylcyclopentadienyl)-(3,5,7-trimethyl-1-adamantylamido)titanium dimethyl;
1,2-dimethylethylene(tetramethylcyclopentadienyl)-(3-fluoro-1-adamantylamido)titanium dimethyl;
1,2-dimethylethylene(tetramethylcyclopentadienyl)-(4tricyclo[2.2.1.0$^{2,6}$]heptylamido)titanium dimethyl;
1,2-dipropylethylene(tetramethylcyclopentadienyl)-(1-adamantylamido)titanium dimethyl;
1,2-dipropylethylene(tetramethylcyclopentadienyl)-(3-noradamantanylamido)titanium dimethyl;
1,2-dipropylethylene(tetramethylcyclopentadienyl)-(3,5-dimethyl-1-adamantylamido)titanium dimethyl;
1,2-dipropylethylene(tetramethylcyclopentadienyl)-(3-methyl-1-adamantylamido)titanium dimethyl;
1,2-dipropylethylene(tetramethylcyclopentadienyl)-(3,5,7-trimethyl-1-adamantylamido)titanium dimethyl;
1,2-dipropylethylene(tetramethylcyclopentadienyl)-(3-fluoro-1-adamantylamido)titanium dimethyl;
1,2-dipropylethylene(tetramethylcyclopentadienyl)-(4-tricyclo[2.2.1.0$^{2,6}$]heptylamido)titanium dimethyl;
2,2-dimethylethylene(tetramethylcyclopentadienyl)-(1-adamantylamido)titanium dimethyl;
2,2-dimethylethylene(tetramethylcyclopentadienyl)-(3-noradamantanylamido)titanium dimethyl;
2,2-dimethylethylene(tetramethylcyclopentadienyl)-(3,5-dimethyl-1-adamantylamido)titanium dimethyl;
2,2-dimethylethylene(tetramethylcyclopentadienyl)-(3-methyl-1-adamantylamido)titanium dimethyl;
2,2-dimethylethylene(tetramethylcyclopentadienyl)-(3,5,7-trimethyl-1-adamantylamido)titanium dimethyl;
2,2-dimethylethylene(tetramethylcyclopentadienyl)-(3-fluoro-1-adamantylamido)titanium dimethyl;
2,2-dimethylethylene(tetramethylcyclopentadienyl)-(4-tricyclo[2.2.1.0$^{2,6}$]heptylamido)titanium dimethyl;
2,2-dipropylethylene(tetramethylcyclopentadienyl)-(1-adamantylamido)titanium dimethyl;
2,2-dipropylethylene(tetramethylcyclopentadienyl)-(3-noradamantanylamido)titanium dimethyl;
2,2-dipropylethylene(tetramethylcyclopentadienyl)-(3,5-dimethyl-1-adamantylamido)titanium dimethyl;
2,2-dipropylethylene(tetramethylcyclopentadienyl)-(3-methyl-1-adamantylamido)titanium dimethyl;
2,2-dipropylethylene(tetramethylcyclopentadienyl)-(3,5,7-trimethyl-1-adamantylamido)titanium dimethyl;
2,2-dipropylethylene(tetramethylcyclopentadienyl)-(3-fluoro-1-adamantylamido)titanium dimethyl;
2,2-dipropylethylene(tetramethylcyclopentadienyl)-(4tricyclo[2.2.1.0$^{2,6}$]heptylmido)titanium dimethyl;
1,1-diphenylethylene(tetramethylcyclopentadienyl)-(1-adamantylamido)titanium dimethyl;
1,1-diphenylethylene(tetramethylcyclopentadienyl)-(3-noradamantanylamido)titanium dimethyl;
1,1-diphenylethylene(tetramethylcyclopentadienyl)-(3,5-dimethyl-1-adamantylamido)titanium dimethyl;
1,1-diphenylethylene(tetramethylcyclopentadienyl)-(3-methyl-1-adamantylamido)titanium dimethyl;
1,1-diphenylethylene(tetramethylcyclopentadienyl)-(3,5,7-trimethyl-1-adamantylamido)titanium dimethyl;
1,1-diphenylethylene(tetramethylcyclopentadienyl)-(3-fluoro-1-adamantylamido)titanium dimethyl;
1,1-diphenylethylene(tetramethylcyclopentadienyl)-(4-tricyclo[2.2.1.0$^{2,6}$]heptylamido)titanium dimethyl;
1,2-diphenylethylene(tetramethylcyclopentadienyl)-(1-adamantylamido)titanium dimethyl;
1,2-diphenylethylene(tetramethylcyclopentadienyl)-(3-noradamantanylamido)titanium dimethyl;
1,2-diphenylethylene(tetramethylcyclopentadienyl)-(3,5-dimethyl-1-adamantylamido)titanium dimethyl;
1,2-diphenylethylene(tetramethylcyclopentadienyl)-(3-methyl-1-adamantylamido)titanium dimethyl;
1,2-diphenylethylene(tetramethylcyclopentadienyl)-(3,5,7-trimethyl-1-adamantylamido)titanium dimethyl;
1,2-diphenylethylene(tetramethylcyclopentadienyl)-(3-fluoro-1-adamantylamido)titanium dimethyl;
1,2-diphenylethylene(tetramethylcyclopentadienyl)-(4tricyclo[2.2.1.0$^{2,6}$]heptylamido)titanium dimethyl;
2,2-diphenylethylene(tetramethylcyclopentadienyl)-(1-adamantylamido)titanium dimethyl;
2,2-diphenylethylene(tetramethylcyclopentadienyl)-(3-noradamantanylamido)titanium dimethyl;
2,2-diphenylethylene(tetramethylcyclopentadienyl)-(3,5-dimethyl-1-adamantylamido)titanium dimethyl;
2,2-diphenylethylene(tetramethylcyclopentadienyl)-(3-methyl-1-adamantylamido)titanium dimethyl;
2,2-diphenylethylene(tetramethylcyclopentadienyl)-(3,5,7-trimethyl-1-adamantylamido)titanium dimethyl;
2,2-diphenylethylene(tetramethylcyclopentadienyl)-(3-fluoro-1-adamantylamido)titanium dimethyl;
2,2-diphenylethylene(tetramethylcyclopentadienyl)-(4-tricyclo[2.2.1.0$^{2,6}$]heptylamido)titanium dimethyl;

The above named specific compounds wherein each Q is methyl are prepared from the corresponding compound wherein each Q is chloro. Thus, specific compounds within Formula V are those wherein each Q is chloro. Also, the corresponding compounds wherein each Q is phenyl, and M is zirconium or hafnium in place of titanium and $(CR^3R^4)_y$ is methylphenylmethylene, tetramethylethylene, tetraethylethylene, propylene, hexamethylpropylene, 1,1-dimethyl propylene, 1,1,2,2-tetramethylpropylene and the like, are also specific compounds within the above Formula V.

The compounds of the present invention can be made using the following general procedure and the specific examples set forth herein.

A lithiated monocyclopentadienyl compound $(C_5H_{5-x}R_x)$Li is reacted with a dihalide of a bridging compound, $R^1R^2TX_2$ wherein X is a halide radical, in a suitable solvent such as tetrahydrofuran. The resulting compound is represented by the formula $(C_5H_{5-x}R_x)TR^1R^2X$.

The compound $(C_5H_{5-x}R_x)TR^1R^2X$ is then reacted with a lithiated amido compound of the formula LiHN-R' in a suitable solvent followed by addition of two equivalants of methyl lithium or similar compound, and subsequent addition of a Group IV metal compound complex such as $MX_4 \cdot 2Et_2O$ wherein M is a metal and X is a halide. The resulting compound is represented by the formula $R^1R^2T(C_5H_{4-x}R_x)(N-R')MX_2$.

The compound $R^1R^2T(C_5H_{4-x}R_x)(N-R')MX_2$ can be utilized as is or it can be converted to the corresponding dihydride, dialkyl, diaryl dicycloalkyl, dialkylaryl, dicycloalkylaryl, dialkylcycloalkyl, or mixtures thereof and the like to utilize with an activator which is not suitable for use when the Q ligands are halide and the like as more fully set forth below.

Monocyclopentadienyl metal compounds of the present invention have been discovered to produce a highly productive catalyst system which produces an ethylene-α-olefin copolymer of significantly greater molecular weight and α-olefin comonomer content as compared with other species of monocyclopentadienyl metal compounds when utilized in an otherwise identical catalyst system under identical polymerization conditions.

All of the above-defined monocyclopentadienyl metal compounds are useful, in combination with an activator or co-catalyst, to polymerize α-olefins or other unsaturated hydrocarbon based monomers including cyclic olefins. Suitable activators include alumoxanes and activators comprising a cation and a non-coordinating compatible anion.

The alumoxane component is an oligomeric compound which may be represented by the general formula $(R^{10}\text{-Al-O})_m$ which is a cyclic compound, or may be $R^{11}(R^{12}\text{Al-O-})_m AlR^{13}_2$ which is a linear compound. An alumoxane is generally a mixture of both the linear and cyclic compounds. In the general alumoxane formula $R^{10}$, $R^{11}$, $R^{12}$ and $R^{13}$ are, independently a $C_1$–$C_5$ alkyl radical, for example, methyl, ethyl, propyl, butyl or pentyl and "m" is an integer from 1 to about 50. Most preferably, $R^{10}$, $R^{11}$, $R^{12}$ and $R^{13}$ are each methyl and "m" is at least 4. When an alkyl aluminum halide is employed in the preparation of the alumoxane, one or more $R^{10-13}$ groups may be halide.

As is now well known, alumoxanes can be prepared by various procedures. For example, a trialkyl aluminum may be reacted with water, in the form of a moist inert organic solvent; or the trialkyl aluminum may be contacted with a hydrated salt, such as hydrated copper sulfate suspended in an inert organic solvent, to yield an alumoxane. Generally, however prepared, the reaction of a trialkyl aluminum with a limited amount of water yields a mixture of both linear and cyclic species of alumoxane.

Suitable alumoxanes utilized in the catalyst systems of this invention are those prepared by the hydrolysis of a trialkylaluminum; such as trimethylaluminum, triethylaluminum, tripropylaluminum; triisobutylaluminum, dimethylaluminumchloride, diisobutylaluminumchloride, diethylaluminumchloride, and the like. The most preferred alumoxane for use is methylalumoxane (MAO). Methylalumoxanes having an average degree of oligomerization of from about 4 to about 25 ("m"=4 to 25), with a range of 13 to 25, are the most preferred.

Modified alumoxanes can also be utilized. Examples of such modified alumoxanes are those disclosed in U.S. Pat. No. 5,041,584; EP 0 516 476; and EP 0 561 476 which are incorporated herein by reference.

Activators comprising a non-coordinating compatible anion component are described in U.S. Pat. No. 5,198,401 which is incorporated herein by reference. Compounds useful as the activator compound, in the preparation of the catalyst comprise a cation, preferably a Bronsted acid capable of donating a proton, and a compatible non-coordinating anion containing a single coordination complex comprising a charge-bearing metal or metalloid core which is relatively large (bulky), capable of stabilizing the active catalyst species (the Group IV-B cation) which is formed when the metallocene and activator compounds are combined, and said anion is sufficiently labile to be displaced by olefinic, diolefinic and acetylenically unsaturated substrates or other neutral Lewis bases such as ethers, nitrites and the like. It is well known that reactive cations other than Bronsted acids capable of donating a proton are also useful. Examples of such other cations include ferrocenium triphenylcarbonium and triethylsilylinium cations. Any metal or metalloid capable of forming a coordination complex which is resistant to degradation by water (or other Bronsted or Lewis Acids) may be used or contained in the anion of the second activator compound. Suitable metals include, but are not limited to, aluminum, gold, platinum and the like. Suitable metalloids include, but are not limited to, boron, phosphorus, silicon and the like.

Compounds containing anions which comprise coordination complexes containing a single metal or metalloid atom are, of course, well known and many, particularly compounds containing a single boron atom in the anion portion, are available commercially. See, for example, U.S. Pat. No. 5,278,119. In light of this, salts containing anions comprising a coordination complex containing a single boron atom are preferred. In general, the second activator compounds useful in the preparation of the catalysts of this invention may be represented by the following general formula:

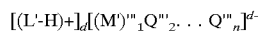

wherein:

L' is a neutral Lewis base;

H is a hydrogen atom;

[L'-H] is a Bronsted acid;

M' is a metal or metalloid;

$Q'''_1$ to $Q'''_n$ are, independently, hydride radicals, bridged or unbridged dialkylamido radicals, alkoxide and aryloxide radicals, hydrocarbyl and substituted hydrocarbyl radicals, halocarbyl and substituted halocarbyl radicals, and hydrocarbyl- and halocarbyl-substituted organometalloid radicals and any one, but not more than one, of $Q_1$ to $Q_n$ may be a halide radical;

m is an integer representing the formal valence charge of M';

n is the total number of ligands Q; and d is an integer representing the total charge on the anion.

Activator compounds comprising boron which are particularly useful in the preparation of catalysts of this invention are represented by the following general formula:

wherein:

L' is a neutral Lewis base;

H is a hydrogen atom;

$[L'-H]^+$ is a Bronsted acid;

B is boron in a valence state of $3^+$;

$Ar_1$ and $Ar_2$ are the same or different substituted-aromatic hydrocarbon radicals and may be linked to each other through a stable bridging group; and $X_3$ and $X_4$ are, independently, hydride radicals, halide radicals, with the proviso that only $X_3$ or $X_4$ will be halide, hydrocarbyl radicals, substituted-hydrocarbyl radicals, halocarbyl radicals, substituted-halocarbyl radicals, hydrocarbyl- and halocarbyl-substituted organometalloid radicals, dialkylamido radicals, and alkoxy and aryloxy radicals.

In general, $Ar_1$ and $Ar2$ may, independently, be any aromatic or substituted-aromatic hydrocarbon radical. Suitable aromatic radicals include, but are not limited to, phenyl, naphthyl and anthracenyl radicals. Suitable substituents on useful substituted-aromatic hydrocarbon radicals, include, but are not necessarily limited to, hydrocarbyl radicals, organometalloid radicals, alkoxy radicals, alkylamido radicals, fluoro and fluorohydrocarbyl radicals and the like such as those useful as $X_3$ or $X_4$. The substituent may be ortho, meta or para, relative to the carbon atom bonded to the boron atom. When either or both $X_3$ and $X_4$ are a hydrocarbyl radical, each may be the same or a different aromatic or substituted-aromatic radical as are $Ar_1$ and $Ar_2$, or the same may be a straight or branched alkyl, alkenyl or alkynyl radical, a cyclic hydrocarbon radical or an alkyl-substituted cyclic hydrocarbon radical. $X_3$ and $X_4$ may also, independently, be alkoxy or dialkylamido radicals, hydrocarbyl radicals and organometalloid radicals and the like. As indicated supra, $Ar_1$ and $Ar_2$ may be linked to each other. Similarly, either or both of $Ar_1$ and $Ar_2$ could be linked to either $X_3$ or $X_4$. Finally, $X_3$ and $X_4$ may also be linked to each other through a suitable bridging group.

Illustrative, but not limiting, examples of boron compounds which may be used as an activator component in the preparation of the improved catalysts of this invention are trialkyl-substituted ammonium salts such as triethylammonium tetra(phenyl)boron, tripropylammonium tetra(phenyl) boron, tri(n-butyl)ammonium tetra(phenyl)boron, trimethylammonium tetra(p-tolyl)boron, trimethylammonium tetra (octolyl)boron, tributylammonium tetra(pentafluorophenyl) boron, tripropylammonium tetra(o,p-dimethylphenyl)boron, tributylammonium tetra(m,m-dimethylphenyl)boron, tributylammonium tetra(p-trifluoromethylphenyl)boron, tributylammonium tetra(pentafluorophenyl)boron, tri(n-butyl) ammonium tetra(o-tolyl)boron and the like; N,N-dialkyl anilinium salts such as N,N-dimethylanilinium tetra(phenyl) boron, N,N-diethylanilinium tetra(phenyl)boron, N,N-2,4,6-pentamethylanilinium tetra(phenyl)boron and the like; dialkyl ammonium salts such as di(isopropyl)ammonium tetra(pentafluorophenyl)boron, dicyclohexylammonium tetra(phenyl)boron, and the like; and triaryl phosphonium salts such as triphenylphosphonium tetra(phenyl)boron, tri (methylphenyl)phosphonium tetra(phenyl)boron, tri (dimethylphenyl)phosphonium tetra(phenyl)boron and the like.

Similar lists of suitable compounds containing other metals and metalloids which are useful as activator components could be made, but such lists are not deemed necessary to a complete disclosure. In this regard, it should be noted that the foregoing list is not intended to be exhaustive and other boron compounds that would be useful as well as useful compounds containing other metals or metalloids would be readily apparent, from the foregoing general equations, to those skilled in the art.

Also useful are neutral Lewis acid ioning activators. An example of such activator is trisperfluorinated phenyl boron ($B[pfp]_3$).

It is important to continued polymerization operations that either the metal cation initially formed from the metallocene, or a decomposition product thereof, be a relatively stable catalyst. It is also important that the anion of the activator compound be chemically stable and bulky. Further, when the cation of the activator component is a Bronsted acid, it is important that the acidity of the activator compound be sufficient, relative to the metallocene, to facilitate the needed proton transfer. Conversely, the basicity of the metal complex must also be sufficient to facilitate the needed proton transfer. In general, metallocenes in which the Q ligands can be hydrolyzed by aqueous solutions can be considered suitable metallocenes for forming the catalysts described herein, because water (our reference Bronsted acid) is a weaker acid than the ammonium ions used as cation in our preferred ion-exchange reagents. This concept allows one of ordinary skill in the art to choose useful metallocene components because stability to water is a basic chemical property easily determined experimentally or by using the chemical literature.

In view of the above, when utilizing an activator comprising a non-coordinating compatible anion, the metal component should be one wherein each Q is selected from the group consisting of hydride and substituted and unsubstituted hydrocarbyl radicals. Preferred Q ligands are hydride, $C_1$–$C_{12}$ alkyl and $C_6$–$C_{12}$ alkaryl and silyl radicals. Most preferred are those Q ligands selected from methyl and benzyl radicals. The preferred metal component species for use with an activator comprising a non-coordinating compatible anion are those set forth above wherein each Q is methyl. Such compounds can be generated in situ by combining a metal component wherein Q is other than a hydride or hydrocarbyl radical with an agent, e.g., any alkylating agent, and optionally, the activator component (e.g., an alumoxane or alkyl aluminum).

In one embodiment of the invention, the chemical reactions which occur upon combination of a monocyclopentadienyl metal compound with a non-coordinating compatible anion activator compound may be represented by reference to the general formulae set forth herein as follows:

Equation I

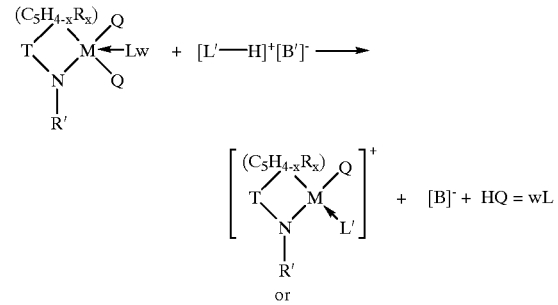

Formula VII

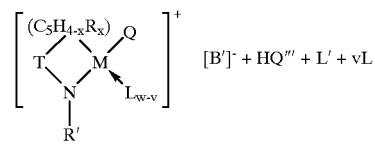

wherein v is an integer $0 \geq v \geq w$ B' represents the anion portion of a compatible activator corresponding to the general formulae set forth in Equation I. When the monocyclopentadienyl metal compound and the non-coordinating compatible anion activator components used to prepare the improved catalysts of the present invention are combined in a suitable solvent or diluent, all or a part of the cation of the activator (the acidic proton) combines with one of the substituents on the metallocene compound. In the case where the metallocene component has a formula corresponding to that of the general formula above, a neutral compound is liberated, which neutral compound either remains in solution or is liberated as a gas. In this regard, it should be noted that if either Q in the metallocene component is a hydride, hydrogen gas may be liberated. Similarly, if either Q is a methyl radical, methane may be liberated as a gas. In the cases where the first component wherein two Q form an alkylidene or cyclometalled hydrocarbyl diradical has a formula corresponding to those of general formulae of the reaction sequence shown directly above, the substituent on the metal is protonated but no substituent is liberated. In general, the rate of formation of the products in the foregoing reaction equations will vary depending upon the choice of the solvent, the acidity of the [L'-H]$^+$ selected, the particular L', the anion, the temperature at which the reaction is completed and the particular monocyclopentadienyl derivative of the metal selected.

As indicated, the improved catalyst compositions of the present invention will, preferably, be prepared in a suitable solvent or diluent. Suitable solvents or diluents include any of the solvents known in the prior art to be useful as solvents in the polymerization of olefins, diolefins and acetylenically unsaturated monomers. Suitable solvents, then, include, but are not necessarily limited to, straight and branched-chain hydrocarbons such as isobutane, butane, pentane, hexane, heptane, octane and the like; cyclic and alicyclic hydrocarbons such as cyclohexane, cycloheptane, methylcyclohexane, methylcycloheptane and the like and, particularly aromatic and alkyl-substituted aromatic compounds such as benzene, toluene, xylene and the like. Suitable solvents also include liquid olefins which may act as monomers or comonomers including ethylene, propylene, butadiene, cyclopentene, hexene, 3-methyl-1-pentene, 4methyl-1-pentene, 1,4-hexadiene, 1-octene, 1-decene and the like. Suitable solvents further include basic solvents which are not generally useful as polymerization solvents when conventional Ziegler-Natta type polymerization catalysts are used such as chlorobenzene.

Catalysts of this invention which are highly productive may be prepared at ratios of monocyclopentadienyl metal compound to non-coordinating compatible anion activator of 10:1 to about 1:1, preferably about 3:1 to 1:1.

With respect to the combination of a monocyclopentadienyl metal compound and non-coordinating compatible anion activator compound to form a catalyst of this invention, it should be noted that the two compounds combined for preparation of the active catalyst must be selected so as to avoid transfer of a fragment of the activator compound anion, particularly an aryl group, to the monocyclopentadienyl metal cation, thereby forming a catalytically inactive species. When anions consisting of hydrocarbyl anions are used, there are several means of preventing anion degradation and formation of inactive species. One method is to carry out the protonolysis process in the presence of small Lewis bases such as tetrahydrofuran. Discrete complexes can be isolated from these reactions, but the Lewis base is insufficiently labile to be displaced readily by olefin monomers, resulting in, at best, catalysts of very low activity. Another method of avoiding deleterious anion degradation is by steric hindrance. Anions of the second component which contain aryl groups can be made more resistant to degradation by introducing substituents in the ortho positions of the phenyl rings. While active metallocene polymerization catalysts can be generated by this method, the complex reaction chemistry often prevents characterization of the catalytically active species. Steric hindrance can also result from substitutions on the cyclopentadienyl rings of the monocyclopentadienyl metal compound component. Hence, wherein the mono(cyclopentadienyl) metal compound used is a [peralkyl-substituted monocyclopentadienyl] Group IVB metal compound, the high degree of substitution on the cyclopentadienyl ring creates sufficient bulkiness that the Lewis base generated by the protonolysis reaction may not coordinate to the metal. Also polyarylborate anions without substituents on the aryl rings may not transfer aryl fragments to generate catalytically inactive species.

Another means of rendering the anion of the activator compound more resistant to degradation is afforded by fluoride substitution, especially perfluoro substitution, in the anion thereof. One class of suitable non-coordinating anions can be represented by the formula $[B(C_6F_5)_3Q''']$ where $Q'''$ is a monoanionic non-bridging radical as described above. The preferred anion of the activator compound of this invention, tetra(pentafluorophenyl)boron, hereafter referred to for convenience by the notation $[B(C_6F_5)_4]$, or $[B(pfp)_4]$, is virtually impervious to degradation and can be used with a much wider range of monocyclopentadienyl metal cations, including those without substitution on the cyclopentadienyl rings, than anions comprising hydrocarbyl radicals.

Since this anion has little or no ability to coordinate to the monocyclopentadienyl metal cation and is not degraded by the monocyclopentadienyl metal cation, structures of the ion-pair catalysts using the $[B(pfp)_4]$ anion depend on steric hindrance of substituents on the cyclopentadienyl ring of the substituent on the nitrogen of the amido ligand monocyclopentadienyl metal compound, the nature of the cation of the activator component, the Lewis base liberated from the protonolysis reaction, and the ratio at which the monocyclopentadienyl metal and activator component are combined. Thus, preferred catalyst systems having a non-coordinating compatible ion activator are those compounds of the above Formulas IV–VI, and, specifically, those species set forth above, in combination with $[B(pfp)_4]$. If Lewis bases other than that liberated from the proton transfer process are present, they may complex to the metal to form modified catalysts of this invention.

Catalyst Systems

The catalyst systems employed in the method of the invention comprise a complex formed upon admixture of the metal component with an activator component. The catalyst system may be prepared by addition of the requisite metal component and either one or more alumoxane components or one or more non-coordinating anion components, or a combination of both, to an inert solvent in which olefin polymerization can be carried out by a solution, slurry or bulk phase polymerization procedure. Additional co-catalysts and/or scavenger compounds, e.g., alkyl aluminum or alkyl boron compounds, may also be included.

The catalyst system may be conveniently prepared by placing the selected metal component and the selected activator component, in any order of addition, in an alkane or aromatic hydrocarbon solvent—preferably one which is also suitable for service as a polymerization diluent. Where the hydrocarbon solvent utilized is also suitable for use as a polymerization diluent, the catalyst system may be prepared in situ in the polymerization reactor. Alternatively, the catalyst system may be separately prepared, in concentrated form, and added to the polymerization diluent in a reactor.

Or, if desired, the components of the catalyst system may be prepared as separate solutions and added to the polymerization diluent in a reactor, in appropriate ratios, as is suitable for a continuous liquid phase polymerization reaction procedure. Alkane and aromatic hydrocarbons suitable as solvents for formation of the catalyst system and also as a polymerization diluent are exemplified by, but are not necessarily limited to, straight and branched chain hydrocarbons such as isobutane, butane, pentane, hexane, heptane, octane and the like, cyclic and alicyclic hydrocarbons such as cyclohexane, cycloheptane, methylcyclohexane, methylcycloheptane and the like, and aromatic and alkyl-substituted aromatic compounds such as benzene, toluene, xylene and the like. Suitable solvents also include liquid olefins which may act as monomers or comonomers including ethylene, propylene, 1-butene, hexene and the like.

In accordance with this invention, when the activator is alumoxane, optimum results are generally obtained wherein the Group IV B metal compound is present in the polymerization diluent in a concentration of from about 0.0001 to about 1.0 millimoles/liter of diluent and the alumoxane component is present in an amount to provide a molar aluminum to transition metal ratio of from about 1:1 to about 20,000:1. Where the activator is one comprising a non-coordinating compatible anion and a cation, such activator is present in an amount sufficient to provide a molar ratio of metal component of from 10:1 to about 1:10. Sufficient solvent should be employed so as to provide adequate heat transfer away from the catalyst components during reaction and to permit good mixing.

The catalyst system ingredients—that is, the Group IV B metal component, the activator, and polymerization diluent—can be added to the reaction vessel rapidly or slowly. The temperature maintained during the contact of the catalyst components can vary widely, such as, for example, from $-100°$ to $300°$ C. Greater or lesser temperatures can also be employed. Preferably, during formation of the catalyst system, the reaction is maintained within a temperature of from about $25°$ to $100°$ C., most preferably about $25°$ C.

Polymerization Process

A typical polymerization process of the invention comprises the steps of contacting ethylene and a $C_3$–$C_{20}$ olefin alone, or with other unsaturated monomers including $C_3$–$C_{20}$ olefins, $C_4$–$C_{20}$ diolefins, and/or acetylenically unsaturated monomers with a catalyst comprising, in a suitable polymerization diluent, a monocyclopentadienyl metal compound, as described above, and an activator. The olefin monomers include $\alpha$-olefins as well as cyclic olefins such as, for example, cyclohexene, norborene, alkyl-substituted norborenes and the like. For example, a catalyst comprising a monocyclopentadienyl metal compound as described above and either 1) a non-coordinating compatible anion activator or 2) an alumoxane activator. The alumoxane activator is utilized in an amount to provide a molar aluminum to titanium metal ratio of from about 1:1 to about 20,000:1 or more. The non-coordinating compatible anion activator is utilized in an amount to provide a molar ratio of monocyclopentadienyl metal compound to non-coordinating anion of 10:1 to about 1:10. The above reaction is conducted by reacting such monomers in the presence of such catalyst system at a temperature of from about $-100°$ C. to about $300°$ C. preferably $20°$ C. to $250°$ C., most preferably from $50°$ C. to $200°$ C. for a time of from about 1 second to about 10 hours to produce a copolymer having a weight average molecular weight of from about 1,000 or less to about 5,000,000, preferably 1,000 to 1.5 million, and a molecular weight distribution of from about 1.5 to about 15.0, preferably less than 5 and most preferably less than 4.

In a preferred embodiment of the process of this invention the catalyst system is utilized in the liquid phase (slurry, solution, suspension or bulk phase or combination thereof, high pressure fluid phase or gas phase polymerization of an olefin monomer. When utilized in a gas phase, slurry phase or suspension phase polymerization, the catalyst systems will preferably be supported catalyst systems. See also, for example, U.S. Pat. No. 5,057,475, WO 94/03506, which is incorporated herein by reference. Such catalyst systems can also be utilized in a gas phase process without a support as described in U.S. Pat. No. 5,317,036. Such catalyst systems can also include other well known additives such as, for example, scavengers. See, for example, U.S. Pat. No. 5,153,157 and WO 94/07927 (Apr. 14, 1994) which are incorporated herein by reference. These processes may be employed singularly or in series. The liquid phase process comprises the steps of contacting an ethylene and an olefin monomer with the catalyst system in a suitable polymerization diluent and reacting the monomers in the presence of the catalyst system for a time and at a temperature sufficient to produce an ethylene-$\alpha$-olefin copolymer of high molecular weight.

The monomers for such process comprise ethylene in combination with an $\alpha$-olefin having 3 to 20 carbon atoms, preferably 3 to 10 carbon atoms, most preferably 3 to 8 carbon atoms, for the production of an ethylene-$\alpha$-olefin copolymer. It should be appreciated that the advantages as observed in an ethylene-$\alpha$-olefin copolymer produced with a catalyst system of this invention would also be expected to be obtained in a copolymer of different $\alpha$-olefins wherein ethylene is not used as a monomer as viewed in comparison to a copolymer of the same or different $\alpha$-olefins produced under similar polymerization conditions with a catalyst system which does not use a monocyclopentadienyl Group IV B metal compound as defined herein. Accordingly, although this invention is described with reference to an ethylene-$\alpha$-olefin copolymer and the advantages of the defined catalyst system for the production thereof, this invention is not to be understood to be limited to the production of an ethylene-$\alpha$-olefin copolymer, but instead the catalyst system hereof is to be understood to be advantageous in the same respects to the production of a copolymer composed of two or more $C_3$ or higher $\alpha$-olefin monomers. Copolymers of higher $\alpha$-olefin such as propylene, butene, styrene or higher $\alpha$-olefins, cyclic olefins and diolefins can also be prepared. Conditions most preferred for the homo- or copolymerization of ethylene are those wherein ethylene is submitted to the reaction zone at pressures of from about 0.019 psia to about 50,000 psia and the reaction temperature is maintained at from about $-100°$ C. to about $300°$ C. Where the activator is an alumoxane, the aluminum to transition metal molar ratio is preferably from about 1:1 to 20,000 to 1. A more preferable range would be 1:1 to 2000:1. The reaction time is preferably from about 10 seconds to about 4 hours.

Without limiting in any way the scope of the invention, one means for carrying out the process of the present invention for production of a copolymer is as follows: in a stirred-tank reactor liquid $\alpha$-olefin monomer is introduced, such as 1-butene. The catalyst system is introduced via nozzles in either the vapor or liquid phase. Feed ethylene gas is introduced either into the vapor phase of the reactor, or sparged into the liquid phase as is well known in the art. The reactor contains a liquid phase composed substantially of liquid $\alpha$-olefin comonomer, together with dissolved ethylene gas, and a vapor phase containing vapors of all monomers. The reactor temperature and pressure may be controlled via reflux of vaporizing $\alpha$-olefin monomer (autorefrigeration), as well as by cooling coils, jackets, etc. The polymerization rate is controlled by the concentration of catalyst. The ethylene content of the polymer product is determined by the ratio of ethylene to α-olefin comonomer in the reactor, which is controlled by manipulating the relative feed rates of these components to the reactor.

EXAMPLES

In the examples which illustrate the practice of the invention the analytical techniques described below were employed for the analysis of the resulting polyolefin products. Molecular weight determinations for polyolefin products were made by Gel Permeation Chromatography (GPC) according to the following technique. Molecular weights and molecular weight distributions were measured using a Waters 150-CV gel permeation chromatograph equipped with a differential refractive index (DRI) detector. The system was used at 145° C. with 1,2,4-trichlorobenzene as the mobile phase. Three Shodex (Showa Denko America, Inc.) mixed bed columns (AT-80 M/S) were used in series. This general technique is discussed in "Liquid Chromatography of Polymers and Related Materials III", J. Cazes editor, Marcel Dekker, 1981, p. 207, which is incorporated herein by reference. No corrections for column spreading were employed; however, data on generally accepted standards, e.g. National Bureau of Standards Polyethylene 1475 demonstrated that such corrections on Mw/Mn (=MWD) were within 0.1 units. Mw/Mn was calculated from elution times. The numerical analyses were performed using waters Expert Ease software package The following examples are intended to illustrate specific embodiments of the invention and are not intended to limit the scope of the invention.

Experimental Section

All procedures were performed under an inert atmosphere of helium or nitrogen. Solvent choices were often optional, for example, in most cases, either pentane or 30–60 petroleum ether can be interchanged. The lithiated amides were prepared from the corresponding amines and either n-BuLi or MeLi. Published methods for preparing $LiHC_5Me_4$ include C. M. Fendrick et al., *Organometallics* 1984, 3, 819 and F. H. Köhler and K. H. Doll, *Z. Naturforsch* 1982, 376, 144. Other lithiated substituted cyclopentadienyl compounds are typically prepared from the corresponding cyclopentadienyl ligand and n-BuLi or MeLi, or by reaction of MeLi with the proper fulvene. $TiCl_4$ was typically used in its etherated form. The etherate can be prepared by simply adding $TiCl_4$ to ether and filtering off the solid product which is then vacuum dried. $TiCl_4$, amines, silanes, substituted and unsubstituted cyclopentadienyl compounds or precursors, and lithium reagents were purchased from Aldrich Chemical Company or Petrarch Systems. Activator components were purchased or prepared from known literature methods. The transition metal compounds $Me_2Si(Me_4C_5)(N-t-Bu)TiCl_2$ (Compound A) and $Me_2Si(Me_4C_5)(N-c-C_{12}H_{23})TiCO_2$ (Compound C), both of which are used as comparative examples, were prepared as described in U.S. Pat. No. 5,264,405.

Example B—Compound B

Part 1. $C_5Me_4HLi$(10.0 g, 0.078 mol) was slowly added to a $Me_2SiCl_2$ (11.5 ml, 0.095 mol, in 225 ml of tetrahydrofuran (thf) solution). The solution was stirred for one hour to assure a complete reaction. The solvent was then removed in vacuo. Pentane was added to precipitate the LiCl. The mixture was filtered through Celite and the solvent was removed from the filtrate in vacuo. $(C_5Me_4H)SiMe_2Cl$ (15.34 g, 0.071 mol) was recovered as a pale yellow liquid.

Part 2: $(C_5Me_4H)SiMe_2Cl$ (6.0 g, 0.028 mol) was diluted in ~150 ml tfh. $LiHN-C_{10}H_{15}$ (lithiated 1-adamantylamine, 4.38 g, 0.028 mol) was added and the reaction mixture was allowed to stir for two hours. The solvent was removed via vacuum, and ~100 ml of ether was added. To this, 34 ml of MeLi (~1.4 M in ether, 0.048 mol) was added and the reaction mixture was stirred for three hours. The mixture was cooled to −30° C. and $TiCl_4·2Et_2O$ (7.74g, 0.023 mol) was slowly added and the reaction mixture was allowed to stir overnight. The solvent was removed via vacuum and pentane was added. This mixture was filtered through Celite to remove the LiCl. The filtrate was reduced in volume and cooled to −30° C. to induce precipitation of the product. The product was filtered off and washed with cold pentane yielding 1.7 g (3.8 mmol) of the yellow solid, $Me_2Si(Me_4C_5)(N-C_{10}H_{15})TiCl_2$.

Comparative Example D—Compound D

Part 1: $C_5Me_4HLi$ (10.0 g, 0.078 mol) dissolved in 150 ml thf was reacted with $Ph_2SiCl_2$ (19.75 g, 0.078 mol). The solution was stirred for three hours to assure a complete reaction. The solvent was then removed in vacuo. Petroleum ether was added to precipitate the LiCl. The mixture was filtered through Celite and the solvent was removed from the filtrate in vacuo. $(C_5Me_4H)SiPh_2Cl$ (22.0 g, 0.65 mol) was recovered as a pale yellow liquid.

Part 2: LiHN-t-Bu (1.4 g, 0.0177 mol) was slowly added to $(C_5Me_4H)SiPh_2Cl$ (6.0 g, 0.0177 mol) in ~100 ml of thf. After stirring for two hours, the solvent was removed via vacuum and replaced with ~150 ml of ether. Assuming an 85% yield of $(C_5Me_4H)SiPh_2(HN-t-Bu)$ (0.015 mmol), 21 ml of 1.4 M MeLi (0.0294 mmol) was added and allowed to stir for three hours. The solution was then chilled to −30° C. and 4.93 g of $TiCl_4·2Et_2O$ (0.0146 mol) was added. The mixture was stirred overnight under ambient conditions.

Isolation of the product involved removing the solvent from the reaction mixture, adding pentane and filtering the mixture to remove the LiCl byproduct. The pentane filtrate was reduced in volume and the solution was chilled to −30° C. to induce crystallization. The product was filtered off, washed with cold pentane, and dried to give 1.8 g of the yellow solid, $Ph_2Si(C_5Me_4)(N-t-Bu)TiCl_2$ (3.7 mmol).

Example E—Compound E

Part 1: $(C_5Me_4H)SiPh_2Cl$ was prepared as described in Example D, Part 1.

Part 2: $LiHN-C_1OH_{15}$ (lithiated 1-adamantylamine, 2.78 g, 0.0177 mol) was slowly added to $(C_5Me_4H)SiPh_2Cl$ (6.0 g, 0.0177 mol) in ~100 ml of thf. After stirring for two hours, the solvent was removed via vacuum and replaced with ~150 ml of ether. Assuming an 85% yield of $(C_5Me_4H)SiPh_2Cl(HN-C_{10}H_{15})$ (0.015 mmol), 21.4 ml of 1.4 M MeLi (0.030 mmol) was added and allowed to stir for three hours. The solution was then chilled to −30° C. and 4.79 g of $TiCl_4·2Et_2O$ (0.0142 mol) was added. The mixture was stirred overnight under ambient conditions.

Isolation of the product involved removing the solvent from the reaction mixture, adding pentane and filtering the mixture to remove the LiCl byproduct. The pentane filtrate was reduced in volume and the solution was chilled to −30° C. to induce crystallization. The product was filtered off, washed with cold pentane and methylene chloride, and dried to give 3.2 g of the mustard yellow solid, $Ph_2Si(C_5Me_4)(N-C_{10}H_{15})TiCl_2$ (5.6 mmol).

Comparative Example F—Compound F

Part 1: ($C_5Me_4H$)$SiPh_2Cl$ was prepared as described in Example D, Part 1.

Part 2: LiHN-c-$C_{12}H_{23}$ (lithiated cyclododecylamine, 3.35 g, 0.0177 mol) was slowly added to ($C_5Me_4H$)$SiPh_2Cl$ (6.0 g, 0.0177 mol) in ~150 ml of thf. After stirring for two hours, the solvent was removed via vacuum and replaced with ~150 ml of ether. Assuming an 85 % yield of ($C_5Me_4H$)$SiPh_2Cl$(HN-c-$C_{12}H_{23}$) (0.015 mmol) 22 ml of 1.4 M MeLi (0.031 mmol) was added and allowed to stir for three hours. The solution was then chilled to −30° C. and 4.97 g of $TiCl_4 \cdot 2Et_2O$ (0.0147 mol) was added. The mixture was stirred overnight under ambient conditions.

Isolation of the product involved removing the solvent from the reaction mixture, adding pentane and filtering the mixture to remove the LiCl byproduct. The pentane filtrate was reduced in volume and the solution was chilled to −30° C. to induce crystallization. The product was filtered off, washed with cold pentane, and dried to give 2.8 g of the yellow solid, $Ph_2Si(C_5Me_4)$(N-c-$C_{12}H_{23}$)$TiCl_2$ (4.6 mmol).

Example G—Compound G

Part 1. t-$BuC_5H_4Li$ (10.0 g, 0.084 mol) was slowly added to a $Me_2SiCl_2$ (13.0 g, 0.101 mol, in 60 ml of tetrahydrofuran solution). The solution was stirred for 2 hours to assure a complete reaction. The solvent was then removed in vacuo. Pentane was added to precipitate the LiCl. The mixture was filtered through Celite and the solvent was removed from the filtrate in vacuo. (t-$BuC_5H_4$)$SiMe_2Cl$ (15.9 g, 0.074 mol) was recovered as a pale yellow liquid.

Part 2. (t-$BuC_5H_4$)$SiMe_2Cl$ (6.0 g, 0.028 mol) was diluted in ~125 ml THF. LiHN-$C_{10}H_{15}$ (lithiated 1-adamantylamine, 4.72 g, 0.030 mol) was added and the reaction mixture was allowed to stir for three hours. The solvent was removed via vacuum, and ~150 ml of ether was added. To this, 40.7 ml of MeLi (~1.4 M in ether, 0.057 mol) was added and the reaction mixture was stirred for 3 hours. The mixture was cooled to −30° C. and $TiCl_4 \cdot 2Et_2O$ (9.26 g, 0.027 mol) was slowly added and the reaction mixture was allowed to stir overnight. The solvent was removed via vacuum and pentane was added. This mixture was filtered through Celite to remove the LiCl. The filtrate was reduced in volume and cooled to −30° C. to induce crystallization of the product. The product was filtered off and washed with cold pentane yielding 3.0 g (6.7 mmol) of the yellow solid, $Me_2Si$(t-$BUC_5H_3$)(N-C10H15)TiCl2.

Example H—Compound H

Me2Si(t-BuC5H3)(N-C10H15)TiMe2 was prepared by adding a stoichiometric amount of MeLi (~1.4 M in ether) to Me2Si(t-BuC5H3)(N-C10H15)TiCl2 (1.0 g, 2.24 mmol, Compound G from Example G) suspended in pentane. The solvent was removed via vacuum and pentane was added to precipitate the LiCl which was filtered off. The filtrate was reduced in volume and cooled to −30° C. to precipitate the product. Me2Si(t-BuC5H3)(N-C10H15)TiMe2 (0.36 g, 0.88 mmol) was isolated.

Example I—Compound I

Me2Si(Me4C5)(N-C10H15)TiMe2 was prepared by adding a stoichiometric amount of MeLi (~1.4M in ether) to Me2Si(Me4$C_5$)(N-C10H15)TiCl2 (1.0 g, 2.24 mmol, Compound B from Example B) suspended in ether. The solvent was removed via vacuum and pentane was added to precipitate the LiCl which was filtered off. The filtrate was reduced in volume and cooled to −30° C. to precipitate the product. Me2Si(Me4C5)(N-C10H15)TiMe2 (0.33 g, 0.81 mmol) was isolated.

Polymerization Examples 2, 4 and 6; Comparative Examples 1, 3, 5 and 7

The polymerization reactions were performed in a stirred 1 L steel autoclave reaction vessel which was equipped to perform continuous Ziegler Natta polymerization reactions at pressures up to 2500 bar and temperatures up to 300° C. The reaction system was supplied with a thermocouple and pressure transducer to measure temperature and pressure continuously, and with means to supply continuously purified compressed ethylene and 1-butene, 1-hexene, propylene or any other desired unsaturated comonomer. Equipment for continuously introducing a measured flow of catalyst solution, and equipment for rapidly venting and quenching the reaction, and of collecting the polymer product were also a part of the reaction system. Without the addition of a solvent, the polymerization was performed with a 1.6 molar ratio of 1-butene to ethylene pressurized at 1300 bar. No hydrogen was used. The catalyst solution was prepared by mixing a specified amount of solid transition metal component with a methylalumoxane solution further diluted in toluene under an inert atmosphere. This catalyst solution was continuously fed by a high pressure pump into the reactor at a rate which resulted in the desired reactor temperature of 180° C. The reactor contents were stirred at 1,000 rpm and the reactor mass flow rate used was 40 kg/hr. Exact run conditions including catalysts preparation [transition metal component (TMC) (g), weight percent methylalumoxane (MAO) and volume used (L), total catalyst solution volume prepared (L), and concentration (g TMC/L) and (g MAO/L)], catalyst feed rate (L/hr), polymer production rate (kg polymer/hr), molar Al/M ratio, TMC productivity (kg polymer/g TMC), TMC productivity (kg polymer/mol TMC), catalyst productivity (kg polymer/ g catalyst) and polymer characteristics including weight average MW (daltons), molecular weight distribution (Mw/Mn=MWD), melt index (g/10 minutes at 190° C), weight percent comonomer (determined by 1H NMR), and "catalyst reactivity ratios" (r1) are collected in Table 1. "Catalyst reativity ratios" were calculated as (1-butene/ethylene molar ratio in reactor-feed) x (ethylene/1-butene molar ratio in the polymer). An example of how to use the information contained in Table 1 follows using Example 1.

Using the reactor design as described above, and using a molar ratio of 1-butene to ethylene of 1.6 without the addition of a solvent, the temperature of the cleaned reactor containing ethylene and 1-butene was equilibrated at the desired reaction temperature of 180° C. The catalyst solution was prepared by mixing 0.878 g of solid compound A with 0.75 L of a 30 weight percent methylalumoxane solution with added toluene to give a total volume of 10L. This catalyst solution was continuously fed by a high pressure pump into the reactor at a rate of 0.84 L/hr which resulted in a temperature of 180° C in the reactor. During this run, ethylene and 1-butene were pressured into the autoclave at a total pressure of 1300 bar. The reactor contents were stirred at 1,000 rpm, and the mass flow rate through the reactor was 40 kg/hr. The yield of polymer product was 4.3 kg/hr of an ethylene-1-butene copolymer which had a weight average molecular weight of 61,000 daltons, a molecular weight distribution of 3.346, and a comonomer incorporation of 32.4 weight percent butene measured by H NMR. The polymer melt index measured at 190° C was 6.6 g/10 minutes. The catalyst reactivity ratio of ethylene to butene was calculated to be 6.7. Productivities were calculated at 59 kg polymer/g A, 21,600 kg polymer/mol A, and 0.26 kg polymer/g catalyst.

EXAMPLE G: Ionic Invention Catalyst and Polymerization of Cyclic Olefin Copolymer Me2Si(t-BuCp)(N-C10H15)TiMe2 (40.0 mg) (compound G) was weighed out under inert atmosphere and N,N-Dimethylanalinium tetrakis-perfluorophenyl boron, [(DMAH)] [B(pfp)4], activator was added to give a slight molar excess of the transition metal complex. Dry toluene (2 mL) was added by pipette and the mixture allowed to stand with occasional stirring until activation was complete (10 to 20 min.). The resulting mixture was septa sealed and ready for transfer to the reactor via cannula.

Dry toluene (0.8 liter) was transferred to a clean, dry and N2 purged 2 liter autoclave reactor using air sensitive technique. The solvent was stirred under a continued slow N2 purge while the reactor was equilibrated at 60° C. Triisobutylaluminum (TIBA) was added as a scavenger by diluting 0.5 mL of a 1 M solution in toluene with additional toluene (10 to 20 mL) and transferring to the reactor via cannula through the purge port using standard air sensitive technique. Norbornene (53 g) was added to the reactor as a concentrated solution in toluene (86 wt. %) via cannula through the purge port using standard air sensitive technique. The N2 purge was shut off simultaneously as the reactor was sealed. Ethylene gas (1 bar) was added to the reactor until the solution was saturated. (Molar feed ratio Norbornene:Ethylene=3.9:1.) The ethylene regulator and flow controller were set to maintain the 15 psig ethylene pressure with a replenishing flow. The reactor was then quickly vented and 18.0 g of the pre-activated catalyst was added to the reactor via cannula through the purge port. The port was then sealed and the ethylene pressure quickly returned to 15 psig by opening the flow controller. The mixture was stirred at 60° C. for 20 minutes.

The reaction was quenched by rapid venting of the rector and its contents poured into one liter of rapidly stirring acetone. The resulting white solid polymer was washed, separated by filtration, and dried in a vacuum oven overnight (60° C., −30 in. Hg). Copolymer (24.2 g) was obtained that had a glass transition temperature of 85° C., Mw=1,380,000, MWD=1.42.

a) a compound of the formula:

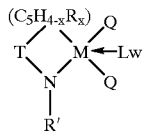

Formula I

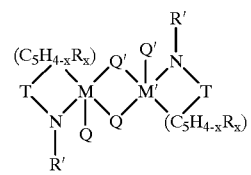

Formula II wherein:

M is Zr, Hf or Ti;

$(C_5H_{4-x}R_x)$ is a cyclopentadienyl ring which is substituted with from zero to four substituent groups R, "x" is 0, 1, 2, 3, or 4 denoting the degree of substitution, and each substituent group R is, independently, a radical selected from the group consisting of $C_1$–$C_{20}$ hydrocarbyl radicals; substituted $C_1$–$C_{20}$ hydrocarbyl radicals wherein one or more hydrogen atoms is replaced by a halogen radical, an amido radical, a phosphido radical, an alkoxy radical, or an aryloxy radical; $C_1$–$C_{20}$ hydrocarbyl-substituted metalloid radicals wherein the metalloid is selected from Group IV A of the Periodic Table of Elements; halogen radicals; amido radicals; phosphido radicals; alkoxy radicals; aryloxy radicals; and alkylborido radicals; or $(C_5H_{4-x}R_x)$ is a cyclopentadienyl ring in which at least two adjacent R-groups are joined together and along with the carbon atoms to which they are attached form a $C_4$-$C_{20}$ ring system;

R' is a radical selected from the group consisting of $C_4$-$C_{30}$ alicyclic hydrocarbyl radicals wherein one or more hydrogen atoms may be replaced by radicals selected from the group consisting of halogen, amido, phosphido, alkoxy, aryloxy and any other radical containing a Lewis acidic or basic functionality, with the proviso that R' is covalently bonded to the nitrogen atom through a tertiary carbon atom;

TABLE 1

| No | TMC | TMC (g) | MAO (Wt. %) | MAO (L) | Total Vol (L) | TMC (g/L) | MAO (g/L) | Feed Rate (L/hr) | Production Rate (kg/hr) | Al/M (molar) | TMC Prod (kg/g) | TMC Prod (kg/mol) | Catalyst Prod (kg/g) | MW | MW D | MI | Wt. % C4 | r1 |
|---|---|---|---|---|---|---|---|---|---|---|---|---|---|---|---|---|---|---|
| C1 | A | 0.878 | 30 | 0.75 | 10 | 0.0878 | 19.6 | 0.84 | 4.3 | 1416 | 59 | 21,601 | 0.26 | 61,000 | 3.346 | 6.6 | 32.4 | 6.7 |
| 2 | B | 0.765 | 30 | 0.60 | 8 | 0.0956 | 19.6 | 0.46 | 3.4 | 1575 | 76 | 33,996 | 0.37 | 88,700 | 3.166 | 2.2 | 34.2 | 6.2 |
| C3 | C | 1.532 | 30 | 1.00 | 20 | 0.0766 | 13.1 | 1.61 | 5.4 | 1405 | 43 | 20,757 | 0.25 | 76,800 | 2.858 | 6.0 | 40.0 | 4.8 |
| 4 | C | 0.513 | 30 | 0.33 | 10 | 0.0513 | 8.6 | 1.59 | 4.1 | 1385 | 50 | 23,758 | 0.29 | 81,800 | 2.967 | 4.7 | 41.1 | 4.6 |
| C5 | D | 1.080 | 30 | 0.70 | 11 | 0.0982 | 16.6 | 1.42 | 4.1 | 1437 | 29 | 14,307 | 0.17 | 59,100 | 3.617 | 7.2 | 38.6 | 5.1 |
| 6 | F | 1.801 | 30 | 1.00 | 18 | 0.1001 | 14.5 | 1.15 | 5.0 | 1426 | 43 | 24,792 | 0.30 | 66,500 | 3.280 | 8.1 | 36.0 | 5.7 |
| C7 | F | 1.547 | 30 | 0.80 | 10 | 0.1547 | 20.9 | 1.72 | 4.4 | 1402 | 16 | 9,880 | 0.12 | 72,600 | 2.825 | 8.3 | 42.4 | 4.3 |

What is claimed is:

1. A method for producing homopolymers of ethylene or copolymers of ethylene and olefins, comprising contacting ethylene and, optionally, one or more of $C_3$–$C_{20}$ olefins and $C_4$–$C_{20}$ diolefins, with a catalyst system prepared by combining:

each Q is independently selected from the group consisting of univalent anionic ligands, both Q together may be an alkylidene or a cyclometallated hydrocarbyl or a divalent anionic chelating ligand; with the proviso that where any Q is a hydrocarbyl such Q is not a substituted or unsubstituted cyclopentadienyl radical;

T is a covalent bridging group containing a Group IV A or V A element;

L is a neutral Lewis base which is optionally covalently bonded to one or both Q;

"w" is a number from 0 to 3; and

M' has the same meaning as M, and Q' has the same meaning as Q; and, b) an activator.

2. The method of claim 1 wherein said olefins include α-olefins, cyclic olefins, and styrene.

3. The method of claim 2 wherein said α-olefins have 3 to 10 carbon atoms.

4. The method of claim 1 wherein M is Ti.

5. The method of claim 1 for producing an ethylene-α-olefin copolymer of greater than 20 wt. % α-olefin content, comprising the steps of:

(a) supplying ethylene and a liquid α-olefin to a reaction zone at a molar ratio of α-olefin to ethylene of less than 2:1 in an amount sufficient to maintain a pressure, within the reaction zone of from about 0.019 to about 50,000 psia; and (b) introducing into contact with the ethylene and α-olefin in the reaction zone said catalyst system.

6. The method of claim 1 for producing an ethylene-α-olefin copolymer of greater than 20 wt. % α-olefin content, comprising the steps of:

(a) supplying ethylene and an α-olefin to a reaction zone at a molar ratio of α-olefin to ethylene of less than 2:1 in an amount sufficient to maintain a pressure within the reaction zone of from about 0.019 to about 50,000 psia; and (b) introducing into contact with the ethylene and α-olefin in the reaction zone said catalyst system;

said catalyst system being introduced in an amount sufficient to maintain a temperature within the reaction zone of from about −100 to about 300° C.

7. The method of claim 1 wherein the activator is a non-coordinating compatible anion and Q is selected from hydride and substituted and unsubstituted $C_1$–$C_{20}$ hydrocarbyl radicals.

8. The method of claim 1 wherein the activator is an alumoxane.

* * * * *